United States Patent
Lin et al.

(10) Patent No.: US 9,833,200 B2
(45) Date of Patent: Dec. 5, 2017

(54) LOW IF ARCHITECTURES FOR NONCONTACT VITAL SIGN DETECTION

(71) Applicant: University of Florida Research Foundation, Inc., Gainesville, FL (US)

(72) Inventors: Jenshan Lin, Gainesville, FL (US); Changyu Wei, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 15/154,324

(22) Filed: May 13, 2016

(65) Prior Publication Data
US 2016/0336989 A1 Nov. 17, 2016

Related U.S. Application Data

(60) Provisional application No. 62/161,359, filed on May 14, 2015.

(51) Int. Cl.
*H04B 1/38* (2015.01)
*A61B 5/00* (2006.01)
(Continued)

(52) U.S. Cl.
CPC ............ *A61B 5/7475* (2013.01); *A61B 5/024* (2013.01); *A61B 5/0507* (2013.01);
(Continued)

(58) Field of Classification Search
CPC . H04B 1/40; H04B 3/23; H04B 1/403; H04B 1/30; H04B 1/28; H04L 27/2601;
(Continued)

(56) References Cited

U.S. PATENT DOCUMENTS 3,796,208 A 3/1974 Bloice
4,085,740 A 4/1978 Allen, Jr.
(Continued)

FOREIGN PATENT DOCUMENTS

EP 1058451 12/2000
GB 2099257 12/1982
(Continued)

OTHER PUBLICATIONS

Blum, T.E., et al., "Advances in Laboratory Modeling of Wave Propagation," Optical Engineering, Oct. 24, 2006, Article No. 10430.
(Continued)

*Primary Examiner* — Zewdu Kassa
(74) *Attorney, Agent, or Firm* — Thomas|Hortsemeyer, LLP.

(57) ABSTRACT

Various examples of methods and systems are provided for vibrational frequency detection (e.g., noncontact vital sign detection) using digitally assisted low intermediate frequency (IF) architectures. In one example, a transceiver system is configured to transmit a modulated signal generated by modulating a local oscillator (LO) signal with an IF carrier; generate an IF signal by down converting a received signal comprising backscatter with the LO signal; and simultaneously sample the IF carrier and the IF signal. A vibration frequency can be determined by demodulating the sampled IF signal with the sampled IF carrier. In another example, a method includes generating and transmitting a modulated signal; receiving backscatter of the modulated signal; generating an IF signal by down converting the received signal with the LO signal; simultaneously sampling the IF carrier and the IF signal; and determining a vibration frequency by demodulating the sampled IF signal with the sampled IF carrier.

20 Claims, 11 Drawing Sheets

(51) Int. Cl.
*H04L 27/00* (2006.01)
*H04L 27/227* (2006.01)
*H04L 27/38* (2006.01)
*A61B 5/05* (2006.01)
*A61B 5/024* (2006.01)

(52) U.S. Cl.
CPC ...... *H04L 27/0002* (2013.01); *H04L 27/2273* (2013.01); *H04L 27/3881* (2013.01)

(58) Field of Classification Search
CPC ... H04L 1/0025; H04L 1/0003; H04L 1/0071; H04L 5/0007; H04L 1/0009; H04L 27/0008; H04L 27/2647; H04L 1/20; H04N 5/4401
USPC .......................................... 375/219, 295, 316
See application file for complete search history.

(56) References Cited

U.S. PATENT DOCUMENTS

| | | |
|---|---|---|
| 4,357,944 A | 11/1982 | Mauser et al. |
| 4,378,698 A | 4/1983 | Masse et al. |
| 4,513,748 A | 4/1985 | Nowogrodzki et al. |
| 5,507,291 A | 4/1996 | Stirbl et al. |
| 5,647,834 A | 7/1997 | Ron |
| 5,694,093 A | 12/1997 | DaSilva et al. |
| 5,867,257 A | 2/1999 | Rice et al. |
| 6,006,188 A | 12/1999 | Bogdashevsky et al. |
| 6,064,383 A | 5/2000 | Skelly |
| 6,132,371 A | 10/2000 | Dempsey et al. |
| 6,188,220 B1 | 2/2001 | Schaefer |
| 6,219,657 B1 | 4/2001 | Hatayama |
| 6,275,806 B1 | 8/2001 | Petrushin |
| 6,480,826 B2 | 11/2002 | Petrushin |
| 6,697,457 B2 | 2/2004 | Petrushin |
| 6,728,679 B1 | 4/2004 | Strubbe et al. |
| 6,768,938 B2 | 7/2004 | McBrien et al. |
| 6,931,341 B2 | 8/2005 | Wakabayashi et al. |
| 7,043,008 B1 | 5/2006 | Dewan |
| 7,073,384 B1 | 7/2006 | Donskoy et al. |
| 7,116,426 B2 | 10/2006 | Lal et al. |
| 7,138,905 B2 | 11/2006 | Pavlidis et al. |
| 7,165,033 B1 | 1/2007 | Liberman |
| 7,272,431 B2 | 9/2007 | McGrath |
| 7,373,301 B2 | 5/2008 | Kemp et al. |
| 7,401,020 B2 | 7/2008 | Eide |
| 7,451,079 B2 | 11/2008 | Oudeyer |
| 7,477,398 B2 | 1/2009 | Lal et al. |
| 7,606,701 B2 | 10/2009 | Degani et al. |
| 7,627,475 B2 | 12/2009 | Petrushin |
| 7,809,117 B2 | 10/2010 | Runge et al. |
| 7,817,082 B2 | 10/2010 | Dwelly et al. |
| 7,848,896 B2 | 12/2010 | Li et al. |
| 7,903,020 B2 | 3/2011 | Lin et al. |
| 7,914,468 B2 | 3/2011 | Shalon et al. |
| 8,052,600 B2 | 11/2011 | Beck et al. |
| 8,239,000 B1 | 8/2012 | Morris et al. |
| 8,306,610 B2 | 11/2012 | Mirow |
| 8,652,040 B2 | 2/2014 | LeBoeuf et al. |
| 8,721,554 B2 | 5/2014 | Lin et al. |
| 8,814,805 B2 | 8/2014 | Lin et al. |
| 9,200,945 B2 | 12/2015 | Lin et al. |
| 9,477,812 B2 | 10/2016 | Lin et al. |
| 2002/0002464 A1 | 1/2002 | Petrushin |
| 2002/0007119 A1 | 1/2002 | Pelissier |
| 2002/0065466 A1 | 5/2002 | Rather et al. |
| 2002/0101568 A1 | 8/2002 | Eberl et al. |
| 2002/0139842 A1 | 10/2002 | Swaine |
| 2003/0028384 A1 | 2/2003 | Kemp et al. |
| 2003/0055654 A1 | 3/2003 | Oudeyer |
| 2003/0069728 A1 | 4/2003 | Tato et al. |
| 2003/0093280 A1 | 5/2003 | Oudeyer |
| 2003/0163311 A1 | 8/2003 | Gong |
| 2003/0182117 A1 | 9/2003 | Monchi et al. |
| 2003/0187660 A1 | 10/2003 | Gong |
| 2003/0208113 A1 | 11/2003 | Mault et al. |
| 2004/0039282 A1 | 2/2004 | Szabo et al. |
| 2004/0123667 A1 | 7/2004 | McGrath |
| 2004/0141417 A1 | 7/2004 | Wakabayashi et al. |
| 2004/0167774 A1 | 8/2004 | Shrivastav |
| 2004/0181143 A1 | 9/2004 | Israel |
| 2004/0249258 A1* | 12/2004 | Tupin, Jr. ............... A61B 5/05 600/407 |
| 2004/0249634 A1 | 12/2004 | Degani et al. |
| 2005/0033127 A1 | 2/2005 | Ciurczak et al. |
| 2005/0073424 A1 | 4/2005 | Ruoss et al. |
| 2005/0088981 A1 | 4/2005 | Woodruff et al. |
| 2005/0128123 A1 | 6/2005 | Greneker, III et al. |
| 2005/0131273 A1 | 6/2005 | Asano et al. |
| 2005/0154264 A1 | 7/2005 | Lecompte et al. |
| 2005/0163302 A1 | 7/2005 | Mock et al. |
| 2005/0171411 A1 | 8/2005 | KenKnight et al. |
| 2006/0028556 A1 | 2/2006 | Bunn et al. |
| 2006/0058694 A1 | 3/2006 | Clark et al. |
| 2006/0064037 A1 | 3/2006 | Shalon et al. |
| 2006/0122834 A1 | 6/2006 | Bennett |
| 2006/0209631 A1 | 9/2006 | Melese et al. |
| 2006/0224046 A1 | 10/2006 | Ramadas et al. |
| 2007/0066916 A1 | 3/2007 | Lemos |
| 2007/0093702 A1 | 4/2007 | Yu et al. |
| 2007/0149883 A1 | 6/2007 | Yesha |
| 2007/0162505 A1 | 7/2007 | Cecchi et al. |
| 2007/0183604 A1 | 8/2007 | Araki et al. |
| 2007/0186165 A1 | 8/2007 | Maislos et al. |
| 2007/0192108 A1 | 8/2007 | Konchitsky |
| 2007/0208569 A1 | 9/2007 | Subramanian et al. |
| 2007/0265531 A1 | 11/2007 | He et al. |
| 2007/0270659 A1 | 11/2007 | Giegerich |
| 2008/0045805 A1 | 2/2008 | Sarel et al. |
| 2008/0045832 A1 | 2/2008 | McGrath |
| 2008/0074307 A1 | 3/2008 | Boric-Lubecke et al. |
| 2008/0077015 A1 | 3/2008 | Boric-Lubecke et al. |
| 2008/0162352 A1 | 7/2008 | Gizewski |
| 2008/0188752 A1 | 8/2008 | Randall et al. |
| 2008/0208015 A1 | 8/2008 | Morris et al. |
| 2008/0215617 A1 | 9/2008 | Cecchi et al. |
| 2008/0238757 A1 | 10/2008 | Lin et al. |
| 2008/0260212 A1 | 10/2008 | Moskal et al. |
| 2008/0269589 A1 | 10/2008 | Thijs et al. |
| 2008/0300805 A1 | 12/2008 | Li et al. |
| 2008/0302187 A1 | 12/2008 | Huber et al. |
| 2009/0063154 A1 | 3/2009 | Gusikhin et al. |
| 2009/0076343 A1 | 3/2009 | James et al. |
| 2009/0128567 A1 | 5/2009 | Shuster et al. |
| 2009/0156907 A1 | 6/2009 | Jung et al. |
| 2009/0176257 A1 | 7/2009 | Bahn et al. |
| 2009/0203972 A1* | 8/2009 | Heneghan ............ A61B 5/0507 600/301 |
| 2009/0216093 A1 | 8/2009 | Sebastian |
| 2009/0292180 A1 | 11/2009 | Mirow |
| 2009/0313019 A1 | 12/2009 | Kato et al. |
| 2010/0083320 A1 | 4/2010 | Roberts et al. |
| 2010/0130873 A1 | 5/2010 | Yuen et al. |
| 2010/0158331 A1 | 6/2010 | Jacobs et al. |
| 2010/0179438 A1 | 7/2010 | Heneghan et al. |
| 2010/0198083 A1 | 8/2010 | Lin et al. |
| 2010/0204587 A1 | 8/2010 | Lin et al. |
| 2010/0205541 A1 | 8/2010 | Rapaport et al. |
| 2010/0226504 A1 | 9/2010 | Watanabe |
| 2010/0241009 A1 | 9/2010 | Petkie |
| 2010/0241010 A1 | 9/2010 | Lin et al. |
| 2010/0281986 A1 | 11/2010 | Toal et al. |
| 2011/0060215 A1 | 3/2011 | Tupin et al. |
| 2011/0183305 A1 | 7/2011 | Orbach |
| 2011/0288379 A1 | 11/2011 | Wu |
| 2012/0022348 A1 | 1/2012 | Droitcour et al. |
| 2015/0241555 A1 | 8/2015 | Lin et al. |
| 2016/0374622 A1 | 12/2016 | Lin et al. |

FOREIGN PATENT DOCUMENTS

| | | |
|---|---|---|
| JP | 2006055504 | 3/2006 |
| JP | 2007-010373 | 1/2007 |

(56) References Cited

FOREIGN PATENT DOCUMENTS

| SU | 1337875 | 9/1987 |
|---|---|---|
| WO | 2004/013611 | 2/2004 |
| WO | 2007/010460 | 1/2007 |
| WO | 2008/151141 | 12/2008 |
| WO | 2009/009690 | 1/2009 |
| WO | 2009/009722 | 1/2009 |
| WO | 2009/076298 | 6/2009 |
| WO | 2010/148141 | 12/2010 |

OTHER PUBLICATIONS

Castellini, P., et al., "Laser Doppler Vibrometry: Development of Advanced Solutions Answering to Technology's Needs," Mechanical Systems and Signal Processing, Aug. 2006, vol. 20, No. 6, pp. 1265-1285.
Ivanov, E.N., et al., "Microwave Interferometry: Application to Precision Measurements and Noise Reductions Techniques," IEEE Transactions on Ultrasonics, Ferroelectrics, and Frequency Control, Nov. 1998, vol. 45, No. 6, pp. 1526-1536.
Kim, S., et al., "On the Development of a Multifunction Millimeter-Wave Sensor for Displacement Sensing and Low-Velocity Measurement," IEEE Transactions on Microwave Theory and Techniques, Nov. 2004, vol. 52, No. 11, pp. 2503-2512.
Lai, S.H.Y., "Engine System Diagnosis Using Vibration Data," Computers and Industrial Engineering, Sep. 1993, vol. 25, Nos. 1-4, pp. 135-138.
Li, C., et al., "Non-Contact Measurement of Periodic Movements by a 22-40GHz Radar Sensor Using Nonlinear Phase Modulation," IEEE/MTT-S International Microwave Symposium, Honolulu, HI, Jun. 2007, pp. 579-582.
MacPherson, W.N., et al., "Multipoint Laser Vibrometer for Modal Analysis," Applied Optics, Jun. 2007, vol. 46, No. 16, pp. 3126-3132.
Stelzer, A., et al., "A Microwave Position Sensor with Sub-Millimeter Accuracy," IEEE Transactions on Microwave Theory and Techniques, Dec. 1999, vol. 47, No. 12, pp. 2621-2624.
Yan, Y., et al., "Effects of I/Q Mismatch on Measurement of Periodic Movement Using a Doppler Radar Sensor," IEEE Radio and Wireless Symposium, 2010, pp. 196-199.
Yan, Y., et al., "Ka-band Quadrature Doppler Radar System with Sub-millimeter Resolution and Sensitivity in Measuring Periodic Movement," 11 1th Annual IEEE Wireless and Microwave Technology Conference, Apr. 2010, pp. 12-13.
Yan, Y., et al., "Wavelength Division Sensing RF Vibrometer," IEEE/MTT-S International Microwave Symposium, Baltimore, MD, Jun. 2011.
Yoshizumi, N., et al., "Multiple-Frequency Ultrasonic Imaging by Transmitting Pulsed Waves of Two Frequencies," Journal of Medical Ultrasonics, Jun. 2009, vol. 36, No. 2, pp. 53-60.
Yan, Y., et al.; Analysis of Detection Methods of RF Vibrometer for Complex Motion Measurement; IEEE Transactions on Microwave Theory and Techniques, vol. 59, No. 12, Dec. 2011; p. 3556-3566.
Cao, Y., et al., "Frequency-Independent Equivalent-Circuit Model for On-Chip Spiral Inductors," IEEE Journal of Solid-State Circuits, Mar. 2003, vol. 38, No. 3, pp. 419-426.
Cao, C., et al., "Millimeter-Wave Voltage-Controlled Oscillators in 0.13-pm CMOS Technology," IEEE Journal of Solid-State Circuits, Jun. 2006, vol. 41, No. 6, pp. 1297-1304.
Chuang, H.R., et al., "60-GHz Millimeter-Wave Life Detection System (MLDS) for Noncontact Human Vital-Sign Monitoring," IEEE Sensors Journal, Mar. 2012, vol. 12, No. 3, pp. 602-609.
Dickson, T.O., et al., "30-100-GHz Inductors and Transformers for Millimeter-Wave (Bi)CMOS Integrated Circuits," IEEE Transactions on Microwave Theory and Techniques, Jan. 2005, vol. 53, No. 1, pp. 123-133.
Jentzsch, A., et al., "Theory and Measurements of Flip-Chip Interconnects for Frequencies up to 100 GHz," IEEE Transactions on Microwave Theory and Techniques, May 2001, vol. 49, No. 5, pp. 871-878.

Kao, T.Y., et al., "Design and Analysis of a 60-GHz CMOS Doppler Micro-radar System-in-Package for Vital Sign and Vibration Detection," IEEE Transactions on Microwave Theory and Techniques, Mar. 2013, vol. 61, No. 4, pp. 1649-1659.
Kao, T.Y., et al., "A Flip-Chip-Packaged and Fully Integrated 60 GHz CMOS Micro-Radar Sensor for Heartbeat and Mechanical Vibration Detections," IEEE Radio Frequency Integrated Circuits Symposium, Jun. 2012, pp. 443-446.
Kraemer, M., et al., "Accurate Electromagnetic Simulation and Measurement of Millimeter-wave Inductors in Bulk CMOS Technology," Proceedings of the 1dh Topical Meeting on Silicon Monolithic Integrated Circuits in RF Systems, Jan. 2010, pp. 61-64.
Kuo, J.L., et al., "A 50 to 70 GHz Power Amplifier Using 90 nm CMOS Technology," IEEE Microwave and Wireless Components Letters, Jan. 2009, vol. 19, No. 1, pp. 45-47.
Laskin E., et al., "Nanoscale CMOS Transceiver Design in the 90-170-GHz Range," IEEE Transactions on Microwave Theory and Techniques, Dec. 2009, vol. 57, No. 12, pp. 3477-3490.
Lee, J., et al., "A Low-Power Low-Cost Fully-Integrated 60-GHz Transceiver System With OOK Modulation and On-Board Antenna Assembly," IEEE Journal of Solid-State Circuits, Feb. 2010, vol. 45, No. 2, pp. 264-275.
Li, C., et al., "High-Sensitivity Software-Configurable 5.8 GHz Radar Sensor Receiver Chip in 0.13 µm CMOS for Non contact Vital Sign Detection," IEEE Transactions on Microwave Theory and Techniques, May 2010, vol. 58, No. 5, pp. 1410-1419.
Liang, C.K., et al., "Systematic Transistor and Inductor Modeling for Millimeter-Wave Design," IEEE Journal of Solid-State Circuits, Feb. 2009, vol. 44, No. 2, pp. 450-457.
Lu, H. C., et al., "Flip-Chip-Assembled W-Band CMOS Chip Modules on Ceramic Integrated Passive Device With Transition Compensation for Millimeter-Wave System-in-Package Integration," IEEE Transactions on Microwave Theory and Techniques, Mar. 2012, vol. 60, No. 3, pp. 766-777.
Pellerano, S., et al., "A 64 GHz LNA With 15.5 dB Gain and 6.5 dB NF in 90 nm CMOS," IEEE Journal of Solid-State Circuits, Jul. 2008, vol. 43, No. 7, pp. 1542-1552.
Petkie, D.T., et al., "Millimeter Wave Radar for Remote Measurement of Vital Signs," IEEE Radar Conference, May 2009, pp. 1-3.
Reynolds, S.K., et al., "A Silicon 60-GHz Receiver and Transmitter Chipset for Broadband Communications," IEEE Journal of Solid-State Circuits, Dec. 2006, vol. 41, No. 12, pp. 2820-2831.
Yan W.S.T., et al., "A 900-MHz CMOS Low-Phase-Noise Voltage-Controlled Ring Oscillator," IEEE Transactions on Circuits and Systems II: Analog and Digital Signal Processing, Feb. 2001, vol. 48, No. 2, pp. 216-221.
Yao, T., et al., "Algorithmic Design of CMOS LNAs and PAs for 60-GHz Radio," IEEE Journal of Solid-State Circuits, May 2007, vol. 42, No. 5, pp. 1044-1057.
Benotsch, E.G., et al. "Rapid Anxiety Assessment in Medical Patients: Evidence for the Validity of Verbal Anxiety Readings," Annals of Behavioral Medicine, 2000, vol. 22, No. 3, pp. 199-203.
Camacho, A., "SWIPE: A Sawtooth Waveform Inspired Pitch Estimator for Speech and Music," Doctoral dissertation, University of Florida, 2007.
Froming, K.B., et al., "Comprehensive Affect Testing System (CATS)", 2006, http://www.psychologysoftware.com/CATS.htm.
Geisheimer, J., et al., "A Non-Contact Lie Detector Using Radar Vital Signs Monitor (RVSM) Technology," IEEE Aerospace and Electronic Systems Magazine, Aug. 2001, vol. 16, No. 8, pp. 10-14.
Gobl, C., et al., "The Role of Voice Quality in Communicating Emotion, Mood and Attitude," Speech Communication, Apr. 2003, vol. 40, Nos. 1-2, pp. 189-212.
Hillenbrand, J., et al., "Acoustic Correlates of Breathy Vocal Quality: Dysphonic Voices and Continuous Speech," Journal of Speech and Hearing Research, Apr. 1996, vol. 39, No. 2, pp. 311-321.
Patel, S., "Acoustic Correlates of Emotions Perceived from Suprasegmental Cues in Speech," Doctoral dissertation, University of Florida, 2009.
Scherer, K.R., "Vocal Affect Expression: A Review and a Model for Future Research," Psychological Bulletin, Mar. 1986, vol. 99, No. 2, pp. 143-165.

(56) References Cited

OTHER PUBLICATIONS

Schroder, M., "Experimental Study of Affect Bursts," Speech Communication, Apr. 2003, vol. 40, Nos. 1-2, pp. 99-116.
Venkatesh, S., et al., "Implementation and Analysis of Respiration-Rate Estimation Using Impulse-Based UWB," IEEE Military Communications Conference, Oct. 17-20, 2005, vol. 5, pp. 3314-3320.
Westbrook, R.A., et al., "The Dimensionality of Consumption Emotion Patterns and Consumer Satisfaction," Journal of Consumer Research, Jun. 1991, vol. 18, No. 1, pp. 84-91.
Xiao, Y., et al., "A Portable Noncontact Heartbeat and Respiration Monitoring System Using 5-GHz Radar", IEEE Sensors Journal, pp. 1042-1043, Jul. 2007, vol. 7, No. 7.
Li, C., et al., "Robust Overnight Monitoring of Human Vital Signs by a Non-Contact Respiration and Heartbeat Detector", 28th IEEE EMBS Annual International Conf., pp. 2235-2238, 2006.
Xiao, Y., et al., "Frequency-Tuning Technique for Remote Detection of Heartbeat and Respiration Using Low-Power Double-Sideband Transmission in the Ka-Band", IEEE Trans. On Microwave Theory and Techniques, pp. 2023-2032, May 2006, vol. 54, No. 5.
Chen, K., et al., "Microwave Life Detection Systems for Searching Human Subjects Under Earthquake Rubble or Behind Barrier", IEEE Trans. On Biomedical Eng., p. 105-114, Jan. 2000, vol. 27, No. 1.
Abramov et al., English Abstract RU 2295911, Mar. 2007.
Li, C. et al., "Complex Signal Demodulation and Random Body Movement Cancellation Techniques for Non-Contact Vital Sign Detection", Microwave Symposium Digest, IEEE MTT-S International, Jun. 2008, pp. 567-570.
Park, B. et al., "Arctangent Demodulation with DC Offset Compensation in Quadrature Doppler Radar Receiver Systems", IEEE Trans. Microwave Theory and Techniques, May 2007, pp. 1073-1079, vol. 55, No. 5.
Li, C. et al., "Design Guidelines for Radio Frequency Non-Contact Vital Sign Detection," Proceedings of the 291th Annual International Conference of the IEEE EMBS, Aug. 2007, pp. 1651-1654.
Li, C. et al., "Optimal Carrier Frequency of Non-Contact Vital Sign Detectors," Proceedings of IEEE Radio and Wireless Symposium, Jan. 2007, pp. 281-284.
Droitcour, A.D. et al., "Range Correlation and I/Q Performance Benefits in Single-Chip Silicon Doppler Radars for Non-Contact Cardiopulmonary Monitoring," IEEE Trans. Microwave Theory and Techniques, Mar. 2004,pp. 838-848, vol. 52, No. 3.
Budge, Jr., M.C. et al., "Range Correlation Effects on Phase and Amplitude Noise", Proc. IEEE Southeast Conf., 1993, pp. 5-9.
Droitcour, A.D., "Non-Contact Measurement of Heart and Respiration Rates with a Single Chip Microwave Doppler Radar," Stanford University, Jun. 2006.
Li, C. et al., "Experiment and Spectral Analysis of a Low-Power Ka-Band Heartbeat Detector Measuring From Four Sides of a Human Body,"IEEE Transactions on Microwave Theory and Techniques, Dec. 2006, pp. 4464-4471, vol. 54, No. 12.
Li, C. et al., "Random Body Movement Cancellation in Doppler Radar Vital Sign Detection," IEEE Transactions on Vlicrowave Theory and Techniques, Dec. 2008, pp. 3143-3152, vol. 56, No. 12.
Xiao, Y. et al., "A Ka-Band Low Power Doppler Radar System for Remote Detection of Cardiopulmonary Motion", Proceedings of the 2005 IEEE Engineering in Medicine and Biology 27th Annual Conference, Sep. 2005, pp. 7151-7154.
Samardzija et al., "Applications of MIMO techniques to Sensing Cardiopulmonary Activity", 2005, pp. 1-4.
Xiao, Y., et al., "Accuracy of a Low-Power Ka-Band Non-Contact Heartbeat Detector Measured from Four Sides of a Human Body," Department of Electrical & Computer Engineering, 2006, pp. 1576-1579.
Lin, "Microwave Doppler Radar Sensor for Detection of Human Vital Signs and Mechanical Vibrations", Feb. 10, 2012. [retrieved on Nov. 19, 2015]. Retrieved from the Internet. <URL: http:I/abe.ufl.edu/research/CRS/seminar/20120210_Lin_Seminar.pdf>.
Pan et al., "A real-time QRS detection algorithm," IEEE Trans. Biomed. Eng., Mar. 1985, vol. 32, No. 3, pp. 230-236.
Razavi, B., "Design Considerations for Direct-Conversion Receivers," IEEE Trans. on Circuits and Systems II: Analog and Digital Signal Processing, Jun. 1997, vol. 44, No. 6, pp. 428-435.
Gu et al., "Instrument-based noncontact Doppler radar vital sign detection system using heterodyne digital quadrature lemodulation architecture," IEEE Trans. Instrum. Meas., Jun. 2010, vol. 59, No. 6, pp. 1580-1588.
Lin, James C. "Noninvasive microwave measurement of respiration." Proceedings of the IEEE 63.10 (Oct. 1975): 1530-1530.
Yavari, Ehsan, and Olga Boric-Lubecke. "Low IF demodulation for physiological pulse Doppler radar." Microwave Symposium (IMS), 2014 IEEE MTT-S International. IEEE, (Jun. 2014).
Gu, Changzhan, et al. "Instrument-based noncontact Doppler radar vital sign detection system using heterodyne digital quadrature demodulation architecture." IEEE Transactions on Instrumentation and Measurement 59.6 (Jun. 2010): 1580-1588.
Mostafanezhad, Isar, and Olga Boric-Lubecke. "Benefits of coherent low-IF for vital signs monitoring using Doppler radar." IEEE Transactions on Microwave Theory and Techniques 62.10 (Oct. 2014): 2481-2487.
Ramachandran, G., and M. Singh. "Three-dimensional reconstruction of cardiac displacement patterns on the chest all during the P, QRS and T-segments of the ECG by laser speckle inteferometry." Medical and Biological ngineering and Computing 27.5 (Sep. 1989): 525-530.
Singh, Megha, and G. Ramachandran. "Reconstruction of sequential cardiac in-plane displacement patterns on the chest wall by laser speckle interferometry." IEEE transactions on biomedical engineering 38.5 (May 1991): 483-489.

* cited by examiner

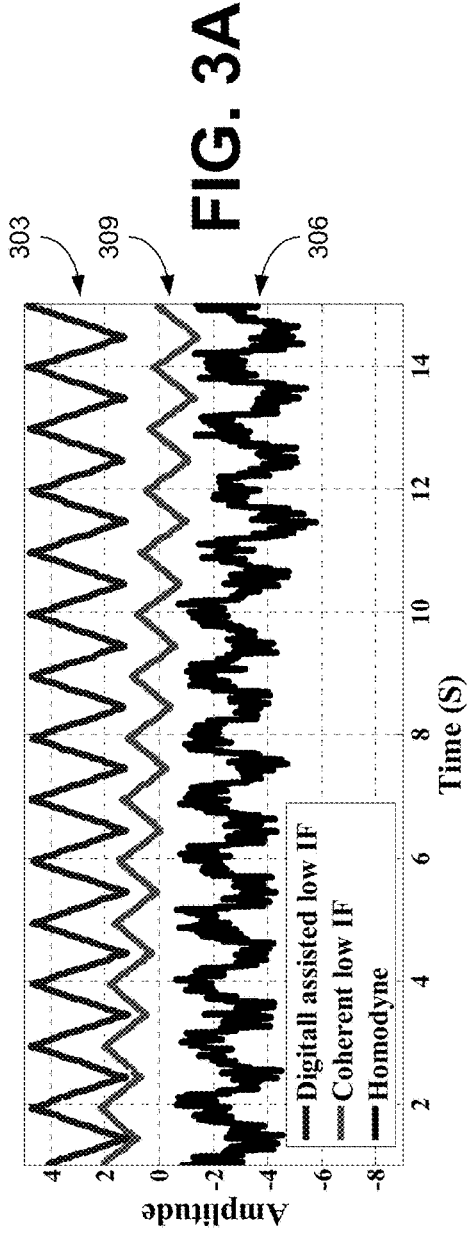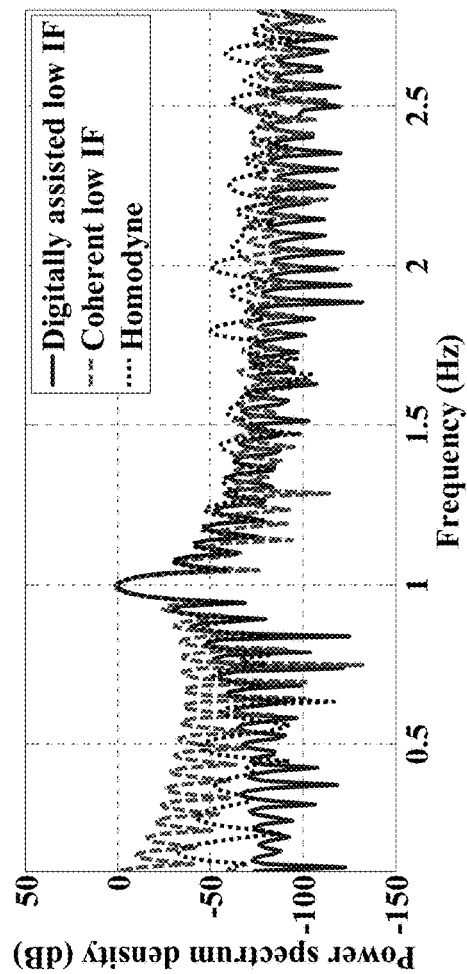

MEASUREMENT RESULTS UNDER DIFFERENT VIBRATION CONDITIONS

| Frequency (Hz) | Amplitude (mm) | Estimated frequency (Hz) | Frequency Error (%) | Estimated amplitude (mm) | Amplitude Error (%) |
|---|---|---|---|---|---|
| 1 | 3 | 0.940 | 6 | 3.21 | 7.1 |
| 1 | 0.5 | 1.007 | 0.7 | 0.528 | 5.6 |
| 0.5 | 15 | 0.496 | 0.8 | 14.0 | 6.7 |
| 0.2 | 0.3 | 0.195 | 2.5 | 0.312 | 4.0 |

LOW IF ARCHITECTURES FOR NONCONTACT VITAL SIGN DETECTION

CROSS-REFERENCE TO RELATED APPLICATIONS

This application claims the benefit of, and priority to, U.S. Provisional Application No. 62/161,359, filed May 14, 2015, which is hereby incorporated herein by reference in its entirety.

BACKGROUND

The research on vital sign detection using noncontact Doppler radar has been carried out since the 1970's. Since then, many methods have been proposed to help to improve the measurement accuracy, lower the noise level and extend the detection range. A receiver with homodyne architecture has been applied to eliminate the detection null points by using both the in-phase and quadrature-phase (I/Q) output. The RF front end also effectively depressed the phase noise from VCO with range correlation effect.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 3A-3B and 4A-4B are plots illustrating comparisons of the digitally assisted low IF system of FIGS. 1A and 1B with other systems in accordance with various embodiments of the present disclosure.

DETAILED DESCRIPTION

Figure 1A:
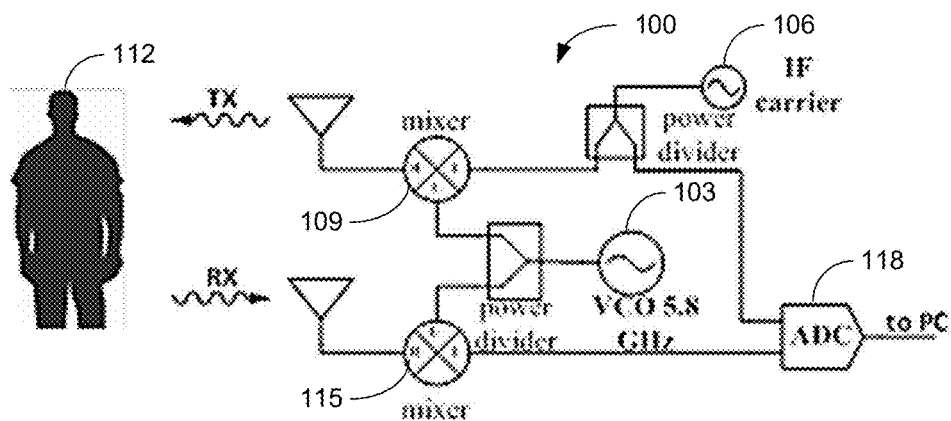
FIGS. 1A and 1B are schematic diagrams of an example of a digitally assisted low IF system in accordance with various embodiments of the present disclosure.

Disclosed herein are various examples related to noncontact vital sign detection using digitally assisted low intermediate frequency (IF) architectures. Reference will now be made in detail to the description of the embodiments as illustrated in the drawings, wherein like reference numbers indicate like parts throughout the several views.

Noncontact Doppler vital sign sensor uses the phase modulated signal backscattered by the subjects to estimate their life sign information. The homodyne architecture can simplify the radar hardware implementation in vital sign detection. However, due to the characteristics of the vital sign signal, the homodyne architecture has some disadvantages in this application scenario.

1) Introduction of DC offset: The homodyne architecture can introduce a DC offset component in the I/Q channel outputs. This could lead to serious distortion on the vital sign signal which is typically a very low frequency signal (0.1 Hz to 1.5 Hz).
2) Susceptibility to low frequency noise: the homodyne architecture directly down converts the vital sign phase information to baseband. The down converted I/Q data will be very vulnerable to low frequency noise, in particular 1/f noise from the mixer and baseband amplifier.

To avoid the aforementioned disadvantages of the homodyne architecture, a heterodyne architecture has been introduced for vital sign detection. In one system, a heterodyne receiver was used for vital sign detection. The system uses a 70 MHz IF carrier and an analog/digital (A/D) converter for digital demodulation. In another system, a coherent low IF heterodyne architecture was proposed. The architecture explores the advantage of range correlation and digitally demodulates the received radar IF signal to achieve a significant improvement of signal to noise ratio (SNR). However, these systems need to know the accurate IF carrier frequency for the digital demodulation, which means the radars will need recalibration if there is an offset of the IF carrier frequency.

In this disclosure, a digitally assisted low IF transceiver system is presented that can provide a 15 dB signal-to-noise ratio (SNR) improvement when compared to the homodyne architecture with the same transmitting power. The low IF transceiver system samples both the IF carrier used in transmission and the received radar IF signal for digital demodulation. The architecture is more tolerant to the IF frequency offset and the phase noise from the IF carrier.

Principles of Digitally Assisted Low IF Transceiver

Referring to FIG. 1A, shown is a schematic diagram of an example of a digitally assisted low IF transceiver system 100, which includes a voltage controlled oscillator (VCO) 103 and an intermediate frequency oscillator (IFO) 106. A transit mixer 109 modulates a local oscillator (LO) signal from the VCO 103 with an IF carrier from the IFO 106. The modulated signal is transmitted toward a target 112 (e.g., a person or other vibrating object) where it is backscattered, and the received signal is down converted by a receive mixer 115. The down converted signal and IF carrier are simultaneously sampled by an analog-to-digital converter (ADC) 118 for demodulation and further processing to determine the condition of the target 112 using processing circuitry (PC), which can include, e.g., a processor and memory. For example, the PC can be a computer, tablet, smart phone, frequency analyzer or other processing device that can determine characteristics of the target 112 from the demodulated output of the ADC 118.

The low IF carrier can be defined as:

$$S_{IF}(t)=A_{IF}\cos(\omega_{IF}t+\phi_{IF}(t)), \quad (1)$$

where $\omega_{IF}$ is the frequency of the IF carrier and $\phi_{IF}(t)$ is the phase noise of the IF carrier. $A_{IF}$ is the amplitude of the IF carrier. The low IF carrier can be used to modulate the LO signal generated from a VCO 103. The modulated signal can be presented as:

$$S_T(t)=A_T\cos((\omega_{LO}+\omega_{IF})t+\phi_{LO}(t)+\phi_{IF}(t)), \quad (2)$$

where $A_T$ is the amplitude of the signal, and $\omega_w$ and $\phi_{LO}(t)$ are the frequency and phase noise of the VCO 103, respectively. The modulated signal $S_T(t)$ is transmitted out and then backscattered from the target 112 and received by the digitally assisted low IF system 100. The received signal can be analyzed as:

$$S_R(t)=A_R\cos((\omega_{LO}+\omega_{IF})(t-t_d)+\phi_{LO}(t-t_d)+\phi_{IF}(t-t_d)+\theta+\phi_V(t)), \quad (3)$$

where $\theta$ is a constant due to the transmission delay and the reflection on the measurement object, $\phi_V(t)$ is the phase variation related to the target's vibration, and $t_d$ is the time delay of the round-trip transmission with $t_d=2d/c$, where d is the distance between the radar and the target 112, c is the speed of light in free space ($c=3.0\times10^8$ m·s$^{-1}$). In a vital sign application, $\phi_V(t)$ is proportional to vibrations such as the subject's chest movement due to heartbeat and respiration.

The received signal $S_R(t)$ can be down converted into an IF signal, which can be represented as:

$$S_{IF}'(t)=A_{IF}'\cos(\omega_{IF}t+\phi_{LO}(t-t_d)-\phi_{LO}(t)+\phi_{IF}(t-t_d)+\theta'+\phi_V(t)), \quad (4)$$

where $\theta'$ is a constant given by $\theta'=\theta-t_d(\omega_{LO}+\omega_{IF})$. Using the range correlation relation $\phi_{LO}(t-t_d)\approx\phi_{LO}(t)$, the down converted signal of Eqn. (4) can be simplified to:

$$S_{IF}'(t)=A_{IF}'\cos(\omega_{IF}t+\phi_{IF}(t-t_d)+\theta'+\phi_V(t)) \quad (5)$$

Since the frequency of $S_{IF}'(t)$ is relatively low (e.g., about 1 kHz in the digitally assisted low IF system 100), it can be directly sampled via an economic A/D converter (ADC) 118.

In the digitally assisted low IF system 100, the ADC 118 samples both $S_{IF}(t)$ and $S_{IF}'(t)$ simultaneously and uses the sampled low IF carrier $S_{IF}(t)$ to demodulate the down converted signal $S_{IF}'(t)$. It can be proved that after the demodulation, the I-channel signal is:

$$I(t)=A_I\cos((\phi_{IF}(t-t_d)-\phi_{IF}(t)+\theta'+\phi_V(t)), \quad (6)$$

where $A_I$ is the amplitude. By using the range correlation $\phi_{IF}(t-t_d)\approx\phi_{IF}(t)$, Eqn. (6) can be reduced to:

$$I(t)=A_I\cos(\theta'+\phi_V(t)), \quad (7)$$

which is the I-channel data without the IF phase noise $\phi_{IF}(t)$. Similarly, we can have Q-channel data as $$Q(t)=A_Q\sin(\theta'+\phi_V(t)), \quad (8)$$

by down converting $S_{IF}'(t)$ with $S_{IF}(t-t_c)$, where $t_c$ is the amount of time to introduce a 90° phase shift for $S_{IF}(t)$, that is $t_c=2\pi/4\omega_{IF}$.

One of the advantages of the digitally assisted low IF architecture of FIG. 1A can be seen in Eqns. (6)-(8). By demodulating the down converted IF signal $S_{IF}'(t)$ with the sampled low IF carrier $S_{IF}(t)$, the phase noise $\phi_{IF}(t)$ is depressed. Low IF systems that use separately generated IF carriers:

$$I_c(t)=\cos(\omega_{IF}'t), \text{ and} \quad (9)$$

$$Q_c(t)=\sin(\omega_{IF}'t) \quad (10)$$

to demodulate the IF signal will get I/Q signals of:

$$I'(t)=\cos(\Delta\omega_{IF}t+\phi_{IF}(t-t_d)+\theta'+\phi_V(t)), \text{ and} \quad (11)$$

$$Q'(t)=A_Q'\sin(\Delta\omega_{IF}t+\phi_{IF}(t-t_d)+\theta'+\phi_V(t)), \quad (12)$$

where $\Delta\omega_{IF}=\omega_{IF}'-\omega_{IF}'$. Thus, those systems would not be able to cancel the phase noise from the IF carrier.

Another advantage of the digitally assisted low IF system 100 can be observed in Eqns. (5)-(8), where the system 100 samples the IF carrier $S_{IF}(t)$ for demodulation and is not affected if the IF carrier frequency $\omega_{IF}$ is different from its nominal value $\omega_{IF}'$. For a coherent IF system however, the IF offset will cause a nonzero $\Delta\omega_{IF}$ as shown in Eqns. (11) and (12). A small $\Delta\omega_{IF}$ (e.g., 0.1 Hz) can introduce an interference within the vital sign frequency range and corrupt the demodulated signal, since the vital sign information $\phi_V(t)$ is a low frequency signal (e.g., typically 0.1 to 1.5 Hz) with a small amplitude.

Figure 1B:
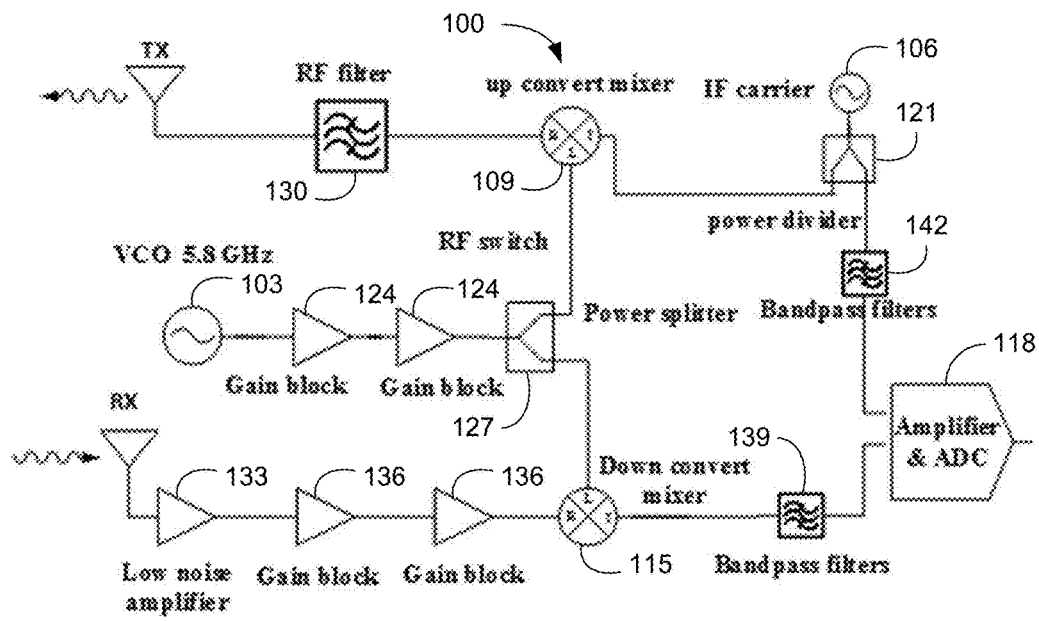

Referring next to FIG. 1B, shown is a more detailed example of the digitally assisted low IF transceiver system 100 of FIG. 1A. The IFO 106 can provide the low IF carrier $S_{IF}(t)$ as presented in Eqn. (1). The $S_{IF}(t)$ is used to modulate the LO signal $S_{LO}(t)$ generated from a VCO 103:

$$S_{LO}(t)=A_{LO}\cos(\omega_{LO}t+\phi_{LO}(t)), \quad (13)$$

where $\omega_{LO}$ is the frequency of the LO signal, $\phi_{LO}(t)$ is the phase noise of the signal, and $A_{LO}$ is the amplitude of the LO signal. The low IF carrier can be provided via a power divider 121 and the LO signal can be provided via one or more gain block 124 and power splitter 127. Signals $S_{LO}(t)$ and $S_{IF}(t)$ are mixed via the up convert mixer 109. The modulated signal $S_M(t)$ can be presented as:

$$S_M(t) = S_{LO}(t) * S_{IF}(t) \quad (14)$$
$$= \frac{A_{IF}A_{LO}}{2}\{\cos[(\omega_{LO}+\omega_{IF})t+\varphi_{LO}(t)+\varphi_{IF}(t)] + \cos[(\omega_{LO}-\omega_{IF})t+\varphi_{LO}(t)-\varphi_{IF}(t)]\}.$$

The double sideband signal $S_M(t)$ is then filtered by a RF filter 130 where the lower frequency component ($\omega_{LO}-\omega_{IF}$) is removed.

The filtered signal $S_T(t)$ of Eqn. (2) is transmitted out toward a target 112 (FIG. 1A). In Eqn. (2), $$A_T = \frac{A_{IF}A_{LO}}{2}$$

is the amplitude of the transmitting signal of the radar. $S_T(t)$ is then backscattered from the target 112. The backscattered signal is received by the radar, and can be processed by a low noise amplifier 133 and one or more gain block 136. The received signal $S_R(t)$ can be presented as Eqn. (3). In a vital sign application, $\phi_V(t)$ is proportional to the subject's chest movement due to heartbeat and respiration. The received signal $S_R(t)$ can be down converted into an IF signal via the down convert mixer 115 using the LO signal $S_{LO}(t)$ from power splitter 127. The down converted IF signal:

$$S_{IF}'(t)=\text{Lowpass}\{S_R(t)*S_{LO}(t)\}, \quad (15)$$

as represented in Eqn. (4). According to the range correlation relation $\phi_{LO}(t-t_d) \approx \phi_{LO}(t)$, Eqn. (4) can be simplified as expressed in Eqn. (5). Since the frequency of $S_{IF}'(t)$ is relatively low, it can be directly sampled via an economic A/D converter 118, which can amplify the signal.

In the digitally-assisted low IF system 100, the signals $S_{IF}(t)$ and $S_{IF}'(t)$ are filtered by bandpass filters 139 and 142 before the A/D sampling 118. The bandpass filtering 139 removes the dc offset in the down converted IF signal and suppresses the high frequency noise. Since the down converted IF signal $S_{IF}'(t)$ is around the IF frequency $\omega_{IF}$, it also suffers from a lower level of 1/f noise from the baseband amplifier. The A/D converter 118 samples both the $S_{IF}(t)$ and $S_{IF}'(t)$ simultaneously and uses the sampled $S_{IF}(t)$ to demodulate $S_{IF}'(t)$. It can be shown that, after the demodulation, the I-channel signal is given by Eqn. (6). Using the range correlation $\phi_{IF}(t-t_d) \approx \phi_{IF}(t)$, Eqn. (6) can be reduced to Eqn. (7), which is the I-channel data without the IF phase noise $\phi_{IF}(t)$. Similarly, the Q-channel data can be reduced to Eqn. (8) by down converting $S_{IF}'(t)$, with $S_{IF}(t-t_c)$ where $t_c$ is the amount of time to introduce a 90° phase shift for $S_{IF}(t)$, that is $t_c = 2\pi/4\omega_{IF}'$.

The advantages of sampling $S_{IF}(t)$ and $S_{IF}'(t)$ simultaneously can be seen by analyzing (6)-(8). By using $S_{IF}(t)$ samples for the demodulation process, the phase noise of the signal $\phi_{IF}(t-t_d)$ can be removed and the synchronization mechanism can be simplified.

Figure 1C:
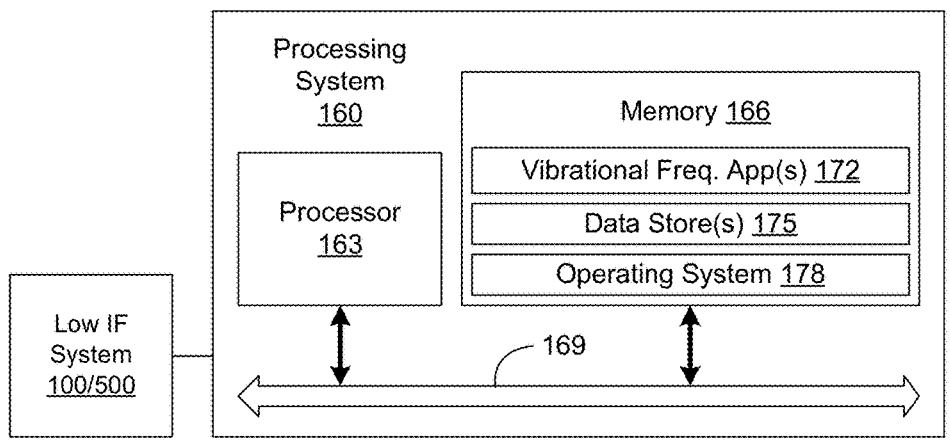
FIG. 1C is a schematic block diagram illustrating an example of processing circuitry that can be used to process the output from the digitally assisted low IF system of FIGS. 1A and 1B of the double sideband low IF system of FIGS. 5A and 5B in accordance with various embodiments of the present disclosure.

FIG. 1C shows an example of a processing system comprising processing circuitry that can be used to analyze the output from the ADC 118 of FIGS. 1A and 1B or FIGS. 5A and 5B. The processing system 160 includes at least one processor circuit, for example, having a processor 163 and a memory 166, both of which are coupled to a local interface 169. To this end, the processing system 160 may comprise, for example, at least one computer, tablet, smart phone, frequency analyzer or like processing device. The local interface 169 may comprise, for example, a data bus with an accompanying address/control bus or other bus structure as can be appreciated. In addition, the processing system 160 include operator interface devices such as, e.g., a display device, a keyboard, and/or a mouse 1918. In some implementations, the operator interface device may be interactive display (e.g., a touch screen) that provides various functionality for operator interaction with the processing system 160. The digitally assisted low IF system 100 can interface with the processing system 160 to allow for acquisition of signal measurements from the ADC 118 (FIGS. 1A and 1B). In some implementations, the digitally assisted low IF system 100 may interface with the processing system 160 via a data acquisition board (DAQ) or other interfacing device.

Stored in the memory 166 are both data and several components that are executable by the processor 163. In particular, stored in the memory 166 and executable by the processor 163 are various application modules or programs such as, e.g., a vibrational frequency module, application, or program 172 for demodulation and/or evaluation of signal measurements from the digitally assisted low IF system 100 using, e.g., an filtering and/or other applications. Also stored in the memory 166 may be a data store 175 and other data. In addition, an operating system 178 may be stored in the memory 166 and executable by the processor 163. It is understood that there may be other applications that are stored in the memory 166 and are executable by the processor 163 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, or other programming languages.

A number of software components are stored in the memory 166 and are executable by the processor 163. In this respect, the term "executable" means a program file that is in a form that can ultimately be run by the processor 163. Examples of executable programs may be, for example, a compiled program that can be translated into machine code in a format that can be loaded into a random access portion of the memory 166 and run by the processor 163, source code that may be expressed in proper format such as object code that is capable of being loaded into a random access portion of the memory 166 and executed by the processor 163, or source code that may be interpreted by another executable program to generate instructions in a random access portion of the memory 166 to be executed by the processor 163, etc. An executable program may be stored in any portion or component of the memory 166 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 166 is defined herein as including both volatile and nonvolatile memory and data storage components. Volatile components are those that do not retain data values upon loss of power. Nonvolatile components are those that retain data upon a loss of power. Thus, the memory 166 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Although the vibrational frequency module, application, or program 172 and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Also, any logic or application described herein, including the vibrational frequency module, application, or program 172 and/or application(s), that comprises software or code can be embodied in any non-transitory computer-readable medium for use by or in connection with an instruction execution system such as, for example, a processor 163 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Experimental Setup

Figure 2:
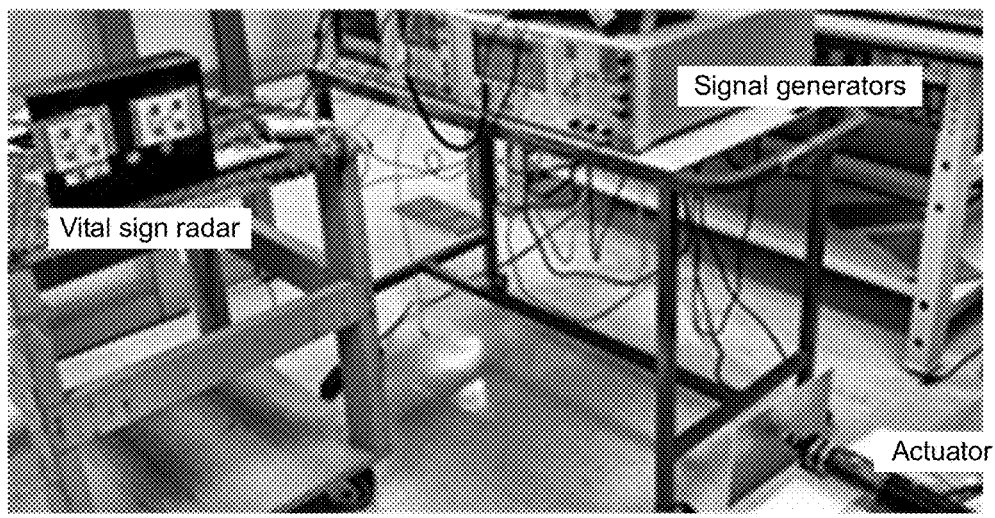
FIG. 2 is an image of an example of a measurement setup for testing of the digitally assisted low IF system of FIGS. 1A and 1B in accordance with various embodiments of the present disclosure.

Referring now to FIG. 2, shown is an example of a measurement setup for testing of various radar systems including the digitally assisted low IF system 100. Three radar systems were implemented to compare their performance: a homodyne architecture, a coherent low IF architecture, and the digitally assisted low IF architecture of FIG. 1. The three systems shared the same implementation on their receiver end: a receiver implemented by an HMC318MS8G low noise amplifier (LNA), an NBB-400 gain block, and an HMC525LC4 I/Q mixer (e.g., receive mixer 115 of FIG. 1). The two low IF systems use HMC219AMS8 as the up conversion mixer (e.g., transmit mixer 109 of FIG. 1). An Agilent E8254A signal generator (e.g., VCO 103 of FIG. 1) generated a 5.8 GHz RF carrier (or LO signal) while an Agilent 33521A function generator (e.g., IFO 106 of FIG. 1) provides the 1 kHz IF carrier. All the systems used the same pair of 2×2 patch array antennas for transmitting and receiving. The down converted signals (the I/Q channel data, the IF carrier, and the IF signal) were amplified via 15× gain baseband amplifiers before sampling. The sampling frequency was 10 kHz. For post processing on a computer, baseband data estimated from all the systems was filtered with a 4th-order Butterworth digital low pass filter (20 Hz bandwidth) before comparison.

Experimental Results

Two sets of experiments were conducted for the comparison. The first group of experiments measured the vibration generated by an actuator (FIG. 2). The second group included measurements on human subjects. The reason of using an actuator as the target 112 (FIG. 1) was that the vibration of an actuator can be accurately controlled to have a repeatable pattern while human vital sign cannot. It was easier to perform a quantitative comparison between the systems by measuring the vibration from an actuator.

In the first set of experiments, the actuator was placed 1.2 m away from the radar (FIG. 2). The transmitted power of the radar systems was set to −10 dBm by adding attenuators at the transmitter side, to demonstrate that the proposed system can detect small vibrations with low power transmissions. The actuator was vibrated at 1 Hz with a peak-to-peak amplitude of 1 mm to emulate human heartbeat movement. The results are shown in FIGS. 3A and 3B. FIG. 3A shows examples of the time domain waveform and FIG. 3B shows examples of the power spectrum density of the different systems. The baseband waveforms and spectrums are normalized for the SNR comparison.

It can be seen from FIG. 3A, the signal (curve 303) from the digitally assisted low IF system 100 (FIG. 1) has a lower noise level when compared to the signal (curve 306) from the homodyne system. The signal (curve 306) from the homodyne system was seriously corrupted by high frequency noise and low frequency DC drift. The digitally assisted low IF system 100 also has a much smaller DC drift when compared to the coherent low IF system (curve 309). The DC drift of the coherent IF system was due to the IF carrier offset $\Delta\omega_w$. The SNR improvement of the digitally assisted low IF system 100 can be observed from FIG. 3B. The proposed system provides a SNR improvement of at least 15 dB when compared to the homodyne system.

Figure 4A:
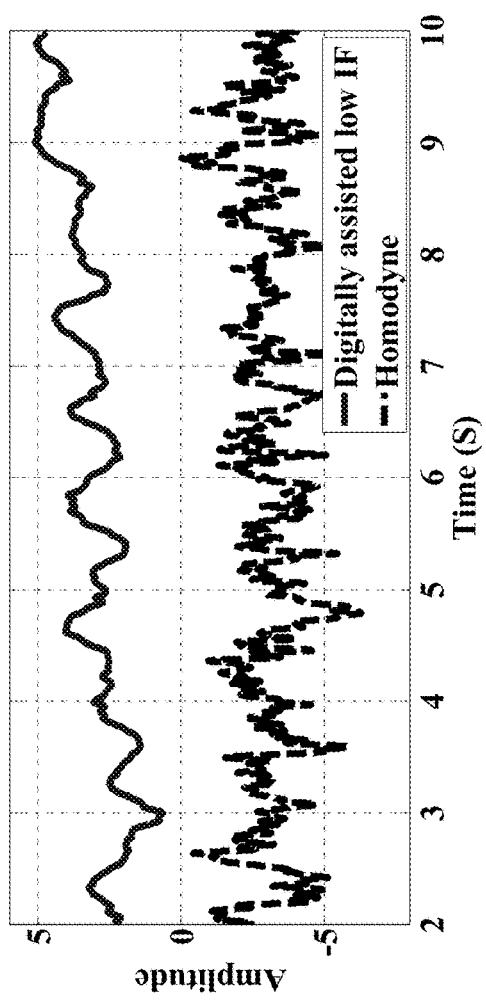
Figure 4B:
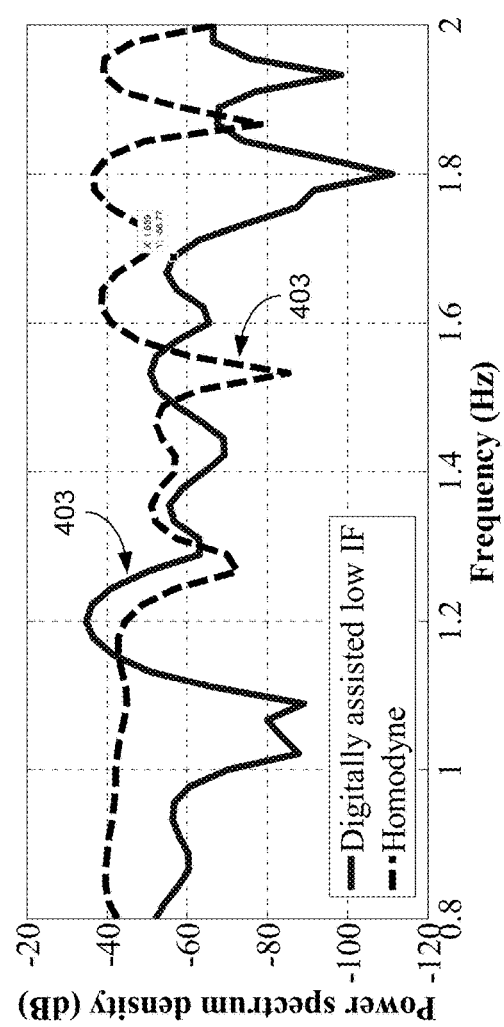

The comparison between the homodyne system and the digitally assisted low IF system 100 on a human test target 112 (FIG. 1) can be seen in FIGS. 4A and 4B. During the test, the subject was seated at 1 m away from the radar sensors and held his/her breath for heartbeat measurements. The transmitted power of the systems was −10 dBm. FIG. 4A shows examples of the time domain waveform and FIG. 4B shows examples of the power spectrum density of the homodyne system and the digitally assisted low IF system 100. The baseband waveforms are normalized for the comparison. It can be seen from curve 403 of FIG. 4B that for the digitally assisted low IF system 100, a peak at 1.2 Hz was detected. This peak corresponds to a heart rate of 72 bpm, consistent with the 70 bpm reference. The homodyne system failed to distinguish a heartbeat peak in its power spectrum density as seen in curve 406.

In this disclosure, a digitally assisted low IF system 100 for vital sign detection application had been presented. The system uses the sampled IF carrier to demodulate the down converted IF signal into the baseband signal. The system 100 simplifies the synchronization mechanism by using the same ADC 118 (FIGS. 1A and 1B) to sample the IF carrier and the down converted IF signal simultaneously. The architecture also eliminates the DC offset and low frequency noise problems existing in a homodyne architecture. At the same time, the digitally assisted low IF system 100 is less sensitive to the IF carrier frequency offset and IF carrier phase noise. Thus, signal degradation due to DC offset and If frequency offset can be avoided. It also improves the SNR by avoiding directly down converting the baseband signal to a DC frequency range. Experiments have been conducted with an actuator and human subjects to verify the performance of the digitally assisted low IF system 100.

Principles of Double Sideband Low IF Transceiver

The digitally assisted low IF system 100 only uses the upper sideband of the up convert signal for transmission, which means that an RF filter 130 (FIG. 1B) is included at the transmitter side to suppress the lower sideband. The design can be simplified by implementing a double sideband low IF system (e.g., a radar system). By using a double sideband RF signal for transmission, the RF filter 130 at the RF front end is no longer needed. A double sideband low IF system can offer a simpler architecture and more design flexibility than the digitally assisted low IF system 100. Instead of using a simple down convert mixer 115 (FIGS. 1A and 1B), an in-phase and quadrature (I/Q) mixer can be used at the receiver side to down convert the reflected RF signal into IF signals. The double sideband architecture continues to avoid DC offset distortion and lower the impact of 1/f noise. An ADC simultaneously samples the IF carrier and the IF signals from the output of the I/Q mixers for synchronization. The digital samples can then be used for digital demodulation. Compared to a direct down convert (DC) system, the double sideband low IF system can measure low frequency vibrations with a better SNR while keeping the hardware implementation simple.

Figure 5A:
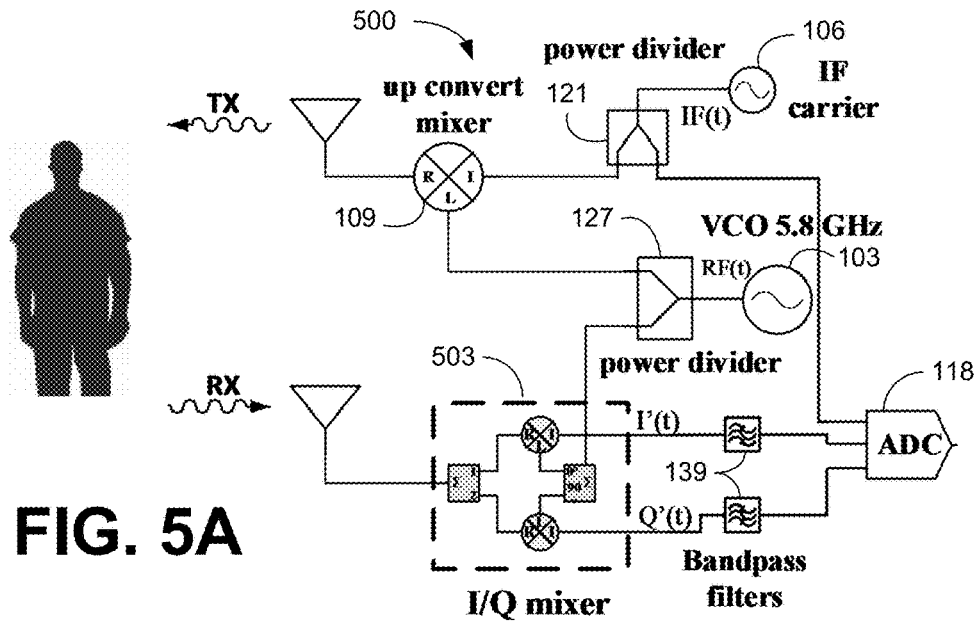
FIGS. 5A and 5B are schematic diagrams of an example of a double sideband low IF system in accordance with various embodiments of the present disclosure.
Figure 5B:
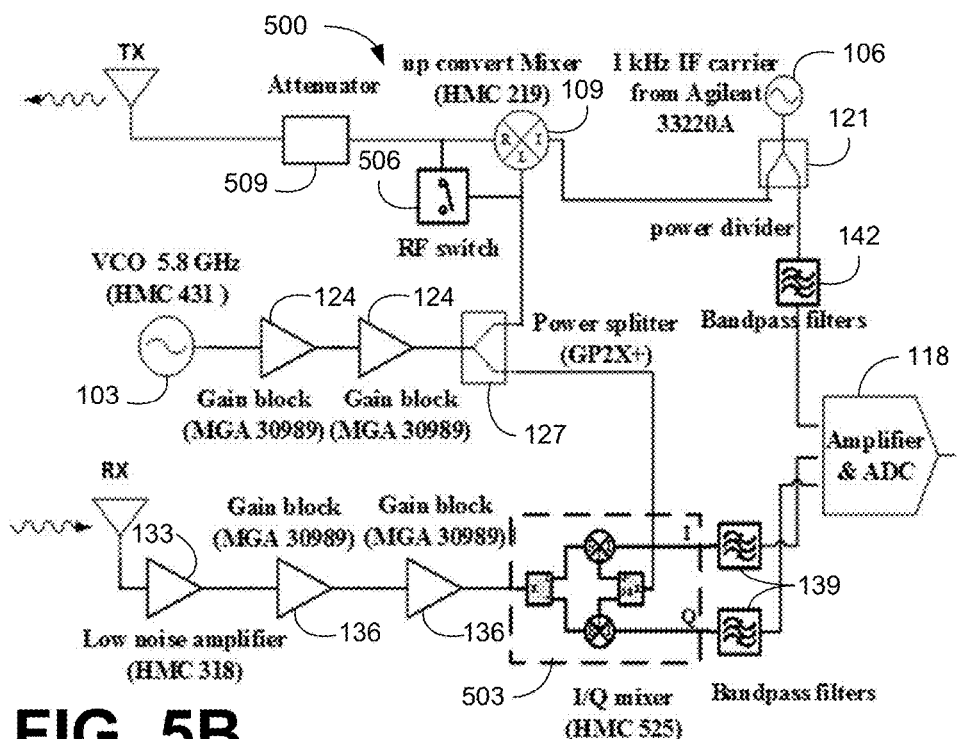

Referring to FIGS. 5A and 5B, shown are schematic diagrams illustrating an example of a double sideband low IF system 500, which can be used for human vital sign measurements or for mechanical vibration measurements. The principles of the double sideband low IF system will now be discussed with respect to the diagrams of FIG. 5A. The VCO 103 generates, e.g., a 5.8 GHz single tone RF signal:

$$RF(t) = A_{RF}\sin(\omega_{RF} t + \phi_{RF}(t)), \quad (16)$$

where $\omega_{RF}$ is the frequency of the RF signal, $A_{RF}$ is the amplitude of the RF signal, and $\phi_{RF}(t)$ is the phase noise of the VCO. RF(t) can be modulated by the IF carrier generated by the IFO 106:

$$IF(t) = A_{IF}\sin(\omega_{IF} t + \phi_{IF}(t)), \quad (17)$$

via the up convert mixer 109. In Eqn. (17), $\phi_{IF}(t)$ is the phase noise of the IF carrier, $\omega_{IF}$ is the frequency of the IF carrier, and $A_{IF}$ is the amplitude. The modulated signal can be presented as:

$$\begin{aligned}RF_M(t) &= RF(t) * IF(t) \\ &= A_M \sin(\omega_{IF} t + \varphi_{IF}(t))\sin(\omega_{RF} t + \varphi_{RF}(t)) \\ &= -\frac{A_M}{2}[\cos((\omega_{RF} + \omega_{IF})t + \varphi_{RF}(t) + \varphi_{IF}(t)) - \\ &\quad \cos((\omega_{RF} - \omega_{IF})t + \varphi_{RF}(t) - \varphi_{IF}(t))],\end{aligned} \quad (18)$$

where $A_M = A_{IF} * A_{RF}$.

The modulated signal $RF_M(t)$ is a double sideband signal that is transmitted out via the TX antenna. The transmitted signal is backscattered from the subject (or object for mechanical vibration measurements), where the backscattered signal $RF_M'(t)$ can be represented as:

$$RF_M'(t) = A_M' \sin(\omega_{IF}(t-t_d) + \phi_{IF}(t-t_d)) * \sin(\omega_{RF}(t-t_d) + \phi_{RF}(t-t_d) + \theta_{RF}), \quad (19)$$

where $\theta_{RF}$ is the phase change due to the reflection on the surface of the subject, $t_d$ is the round-trip time delay of the RF signal, and $A_M'$ is the amplitude. It can be shown that:

$$t_d = \frac{2(d_0 + \Delta d(t))}{c}, \quad (20)$$

where c is the light speed in free space, $d_0$ is the average distance between the subject and the double sideband low IF system 500, and $\Delta d(t)$ is the displacement due to the physiology activities of the subject (or movements of the object for mechanical vibration measurements). It can be shown that $RF_M'(t)$ can also be presented as:

$$RF_M'(t) = -\frac{A_M'}{2}\{\cos(\omega_{RF}^+(t-t_d) + \theta_1) - \cos(\omega_{RF}^-(t-t_d) + \theta_2)\}, \quad (21)$$

where $\omega_{RF}^+ = \omega_{RF} + \omega_{IF}, \omega_{RF}^- = \omega_{RF} - \omega_{IF}, \theta_1 = \phi_{RF}(t-t_d) + \phi_{IF}(t-t_d) + \theta_{RF}$, and $\theta_2 = \phi_{RF}(t-t_d) - \phi_{IF}(t-t_d) + \theta_{RF}$.

From Eqn. (21), it can be seen that the backscattered signal $RF_M'$ is a double sideband signal with two frequency components: $\omega_{RF}^+$ and $\omega_{RF}^-$. The signal $RF_M'(t)$ is received by the RX antenna of the double sideband low IF system 500 and down converted by the I/Q mixer 503. The I/Q mixer 503 down converts $RF_M'(t)$ using the signal RF(t) from the VCO 103 as the LO signal. The down converted I' channel signal can be represented as:

$$\begin{aligned}I'(t) &= \text{Low Pass filtering}\{RF_M'(t) * RF(t)\} \quad (22)\\ &= \frac{A_M' A_{RF}}{4}\{\sin(\omega_{IF} t - \omega_{RF}^+ t_d + \theta_1 - \varphi_{RF}(t)) + \\ &\quad \sin(\omega_{IF} t + \omega_{RF}^- t_d - \theta_2 + \varphi_{RF}(t))\}.\end{aligned}$$

For short distance measurements (e.g., $d_0 < 10$ m), the phase noise $\phi_{RF}(t)$ of the VCO 103 can be treated as a low frequency signal, i.e. $\phi_{RF}(t) \approx \phi_{RF}(t-t_d)$, which allows Eqn. (22) to be further simplified to:

$$I'(t) = \frac{A_M' A_{RF}}{2}\cos(\omega_{RF} t_d - \theta_{RF}) * \sin(\omega_{IF} t - \omega_{IF} t_d + \varphi_{IF}(t - t_d)). \quad (23)$$

The frequency of the IF carrier, $f_{IF}$, in the experiments is around 1 kHz, which means that for short distance measurements the following:

$$\omega_{IF} t_d = \frac{4\pi d}{\lambda_{IF}} \sim 10^{-4}, \quad (24)$$

is a negligible term ($\lambda_{IF}$ is the wavelength of the IF carrier) and $$I'(t) \approx \frac{A_M' A_{RF}}{2}\cos(\omega_{RF} t_d - \theta_{RF}) * \sin(\omega_{IF} t + \varphi_{IF}(t - t_d)). \quad (25)$$

The ADC 118 samples the IF carrier IF(t) from the power divider 121 and the down converted I'(t) from the I/Q mixer 503, and uses the IF(t) to digitally down convert signal I'(t) into the baseband/channel signal:

$$\begin{aligned}I(t) &= \text{Low Pass Filtering}\{I'(t) * IF(t)\} \quad (26)\\ &= \frac{A_M' A_{RF} A_{IF}}{4}\cos(\omega_{RF} t_d - \theta_{RF})\cos\omega_{IF} t_d.\end{aligned}$$

Using the short distance approximation of Eqn. (24), the baseband I channel signal can be approximated as:

$$I(t) \approx \frac{A_M' A_{RF} A_{IF}}{4}\cos(\omega_{RF} t_d - \theta_{RF}). \quad (27)$$

Similarly, the ADC 118 can sample the down converted Q'(t) signal from the I/Q mixer 503 and digitally down convert it into the baseband Q channel signal:

$$Q(t) \approx \frac{A'_M A_{RF} A_{IF}}{2} \sin(\omega_{RF} t_d - \theta_{RF}). \qquad (28)$$

By demodulating the baseband I/Q signals from Eqns. (27) and (28), the phase information can be retrieved as:

$$\psi = \omega_{RF} t_d - \theta_{RF} = \frac{4\pi(d_0 + \Delta d(t))}{\lambda_{RF}} - \theta_{RF}, \qquad (29)$$

where $\lambda_{RF}$ is the wavelength of the RF carrier. The physiology activities of the subject or the displacement of objects $\Delta d(t)$ can then be measured by processing Eqn. (29).

Comparison Between a Direct Down Convert System and a Double Sideband Low IF System.

Non-ideal characteristics of I/Q demodulators like LO leakage can introduce DC offset in the output of the mixers, degrading the low frequency I/Q signals. Another factor that can cause the degradation of signals is the 1/f noise from the mixer and the baseband amplifier. The power level of the 1/f noise is inversely proportional to the frequency, which means signals at low frequency are more vulnerable to 1/f noise.

For a DC radar system, the demodulated I/Q signals can be represented as:

$$I_{DC}(t) = A_{DC} \cos\left(\frac{4\pi(d_0 + \Delta d(t))}{\lambda_{RF}} - \theta_{RF}\right), \text{ and} \qquad (30)$$

$$Q_{DC}(t) = A_{DC} \sin\left(\frac{4\pi(d_0 + \Delta d(t))}{\lambda_{RF}} - \theta_{RF}\right), \qquad (31)$$

From these equations, it can be seen that $\Delta d(t)$ is a low frequency signal corresponding to the low frequency vibrations and vital sign activities. Thus, $I_{DC}(t)$ and $Q_{DC}(t)$ are signals around the DC frequency range. So for a DC radar system, the demodulated I/Q signals suffers strong 1/f noise and is distorted by the DC offset.

In the double sideband low IF system 500, the problems of the DC system can be avoided by down converting the RF signal into the IF frequency range (in the experiments, $\omega_{IF} = 2\pi \ast 10^3$ rad·s$^{-1}$). From Eqn. (25), the I/Q mixer 503 down converts the signals to a frequency around $\omega_w$, which is far away from DC. Thus the low frequency DC offset generated by the I/Q mixer 503 can be easily filtered from signals I'(t) and Q'(t) using bandpass filters 139. The ADC 118 can be used to sample the filtered IF signals I'(t) and Q'(t) for digital demodulation. Signals I'(t) and Q'(t) also have a lower 1/f noise level since the frequency of the signals is far above the DC frequency.

Comparison Between a Double Sideband Low IF System and a Digitally Assisted Low IF Radar System.

A digitally assisted low IF system 100 (FIGS. 1A and 1B) can also help to avoid DC offset and lower the 1/f noise. However, the system 100 uses an RF filter 130 (FIG. 1B) at the transmitter end to generate a single sideband RF signal for transmission. A digitally assisted low IF radar transmits the modulated signal of Eqn. (2) for vibration measurements or vital sign detection. As it is shown in Eqns. (16)-(18), the output of the up convert mixer 109 is a double sideband RF signal which contains two frequency components: components around frequency $\omega_{RF} \pm \omega_{IF}$. To generate the single sideband signal in Eqn. (2), an RF filter 130 is used at the transmitter end to suppress the lower sideband (the component with a frequency around $\omega_{RF} - \omega_{IF}$. The filter 130 can increase the complexity of the radar hardware, since a highly selective RF filter should be used for the lower sideband suppression at the lower sideband frequency, while a high speed ADC 118 should be used for the IF signal sampling at the higher sideband frequency.

For the double sideband low IF system 500, the RF filter 130 is no longer needed since the system 500 transmits a double sideband RF signal for detection. The receiver end can retrieve the vibration information by using an I/Q mixer 503 to down convert the RF signal into signals I'(t) and Q'(t). This helps to simplify the design. In addition, the choice of the IF frequency can be more flexible without concerning the implementation of an RF filter in the double sideband low IF system 500.

Simulation Results.

A simulation is set up in Matlab environment to verify the advantages of the double sideband low IF radar system. The simulation is to compare the SNR of the signals from a double sideband low IF system 500 and a DC system with the presence of 1/f noise.

Figure 6:
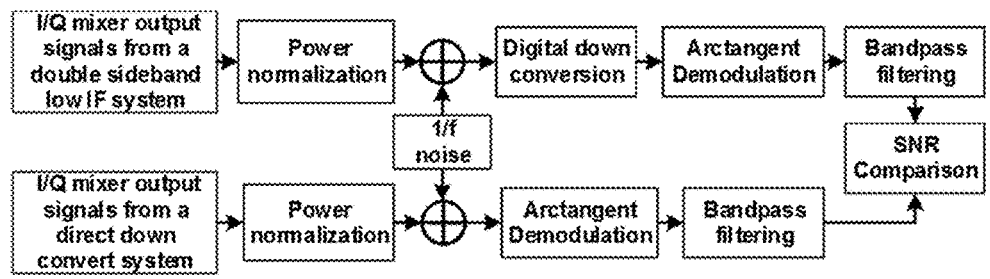
FIG. 6 is a flow diagram illustrating the simulation for the double sideband low IF system of FIGS. 5A and 5B and a direct down convert system in accordance with various embodiments of the present disclosure.
Figure 7:
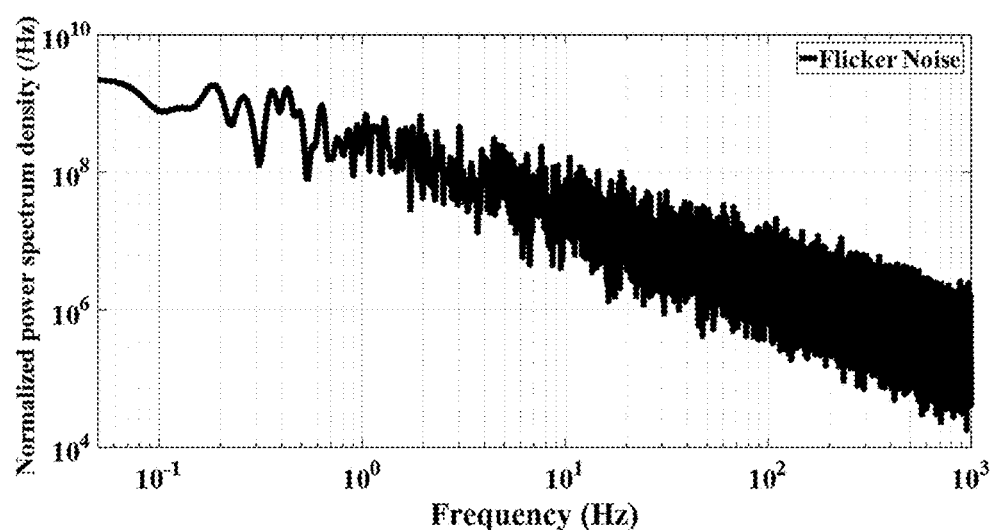
FIGS. 7 and 8A-8B are plots illustrating simulation comparisons of the double sideband low IF system of FIGS. 5A and 5B with other systems in accordance with various embodiments of the present disclosure.

Referring to FIG. 6, shown is a flow diagram illustrating the Matlab 1/f noise simulation for the double sideband low IF system 500 and the direct down convert system. In the simulation, both systems were simulated to measure a 0.2 Hz triangle wave vibration. To simulate the measurement condition in which two radar systems use the same transmitting power and the same receiver chain, the signals from the output of I/Q mixers of the two systems were normalized to the same power level (18.2 dBm). The 1/f noise was added to the signals to simulate the noise in the mixer and the baseband circuits of the radar systems. FIG. 7 shows the power spectrum density of the added noise. It can be seen that the power density of the noise is inversely proportional to the frequency. Eventually, the noisy signals from the two systems were demodulated using an arctangent demodulation method and filtered by the same bandpass filter (0.1 Hz~30 Hz passband) for the SNR comparison.

Figure 8A:
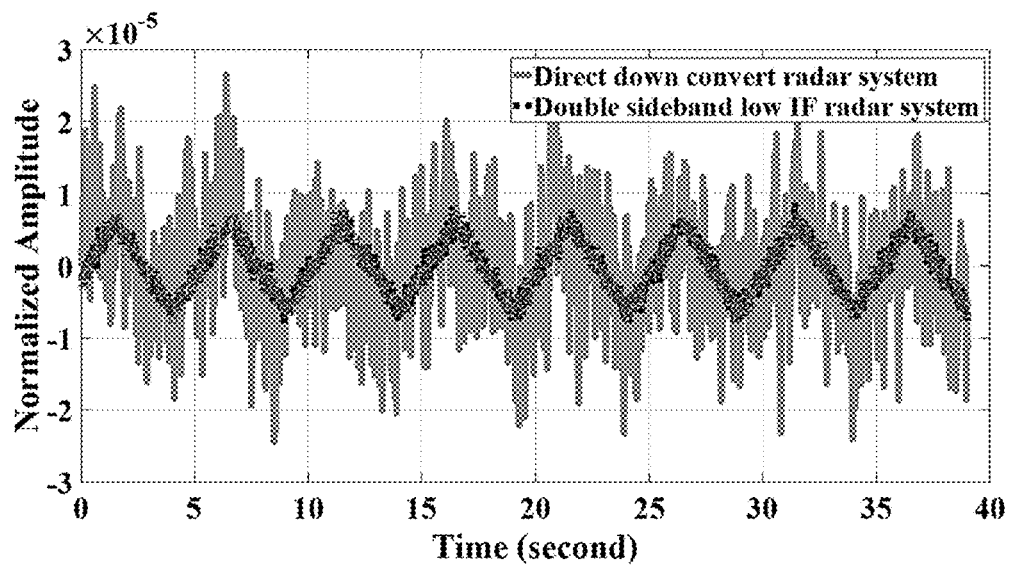
Figure 8B:
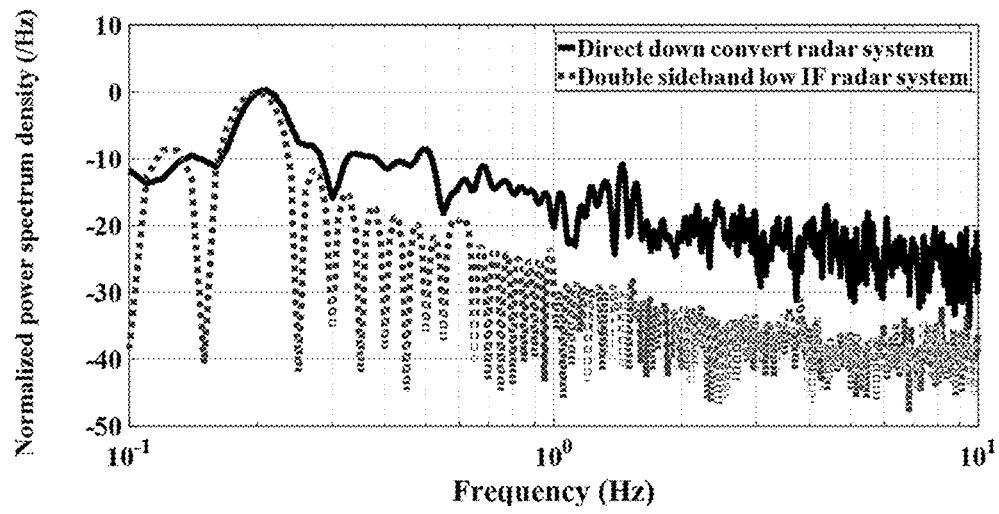

Referring to FIGS. 8A and 8B, shown are the time domain waveforms and the power spectrum density, respectively, of the noise simulation results for the direct down convert system and the double sideband low IF system 500, with the power density spectrums normalized to the power of the triangle signals to compare the SNR. The demodulated waveforms of the simulation are shown in FIG. 8A. It can be seen that the waveform from the double sideband low IF system 500 has a better SNR. This can be further verified from FIG. 8B, where the power spectrum density of the two waveforms are compared. It can be observed that the noise level in the double sideband low IF system 500 is at least 10 dB lower than that of the DC system. This may be attributed to the double sideband low IF system 500 down converting the RF signal to the $f_{IF}$ frequency range (1 kHz for the simulation), while the DC system down converts the RF signal directly to the frequency around DC. The power level of the 1/f noise is much lower at $f_{IF}$ as compared to the frequency around DC (see FIG. 7).

Experimental Setup

FIG. 5B shows an example of the hardware implementation of the double sideband low IF radar system 500 used for the experiments. When the up convert mixer 109 (e.g., HMC 219) is connected to the circuit and the RF switch 506 is off, the system 500 works as a double sideband low IF system. During the experiments, a 1 kHz sinusoidal IF carrier from an Agilent 33220A function generator (acting as an IFO 106) was mixed with the 5.8 GHz RF carrier via the up convert mixer 109. The mixer 109 generated a double sideband radar signal for transmission. When the up convert mixer 109 was disconnected away from the rest of the circuits and the RF switch 506 was turn on, the system worked as a direct down convert radar system. In this case, the single tone RF carrier (5.8 GHz) was transmitted out directly via the RF switch 506. The two radar systems share the same circuits at their RF receiver ends. The loss of the attenuator 509 was adjusted so that under the two configurations, the transmitting power of the system is the same. This setup was consistent with the simulation conditions discussed above.

The baseband bandpass filters 139/142 for the two configurations were different: for the double sideband low IF configuration, the passband was 980 Hz to 1020 Hz; and for the direct down convert configuration, the passband was 0.1 Hz to 40 Hz. So the bandwidth of the filters 139/142 under the two configurations was the same (40 Hz). The bandpass filtered signals (down converted I/Q signals and the IF carrier) were amplified via a baseband amplifier with the same gain (20×) across the two passbands. The signals are then sampled by an ADC 118 (e.g., NI USB-6210). The sampling frequency was 40 kHz for each channel. During post processing by the processing system 160 (FIG. 10), digital demodulation was used to demodulate the I/Q data samples. The demodulated baseband data from the two systems were filtered with a 4th order Butterworth low pass filter (20 Hz bandwidth) before the comparison.

Figure 9:
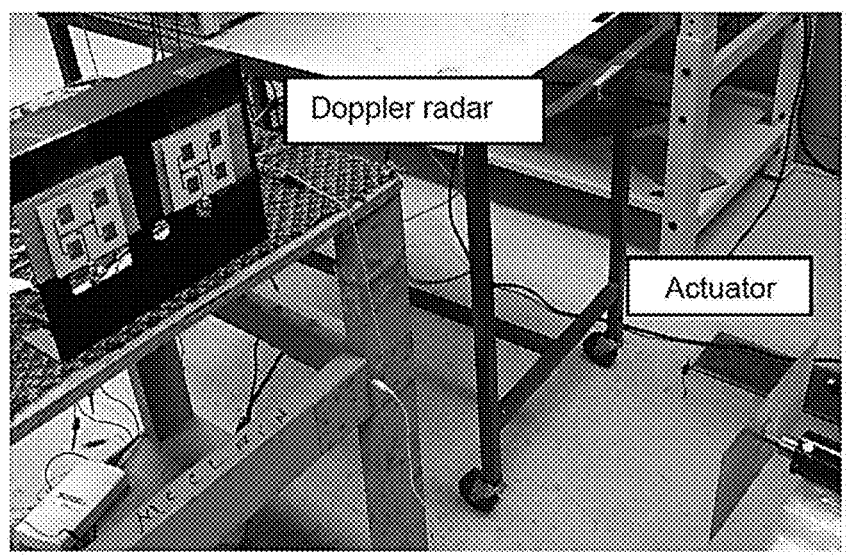
FIG. 9 is an image of an example of a measurement setup for testing of the double sideband low IF system of FIGS. 5A and 5B in accordance with various embodiments of the present disclosure.

FIG. 9 shows the experiment setup for the measurements. The radar system used a pair of 2×2 patch array antennas for transmitting and receiving. An actuator was affixed 1 m away from the antenna array. The actuator was programmed to thrust a 30 mm×50 mm copper plane to generate the vibration movements for the experiments.

Experimental Results

Three groups of experiments were set up to evaluate the performance of the double sideband low IF system 500. First, measurements were conducted to compare the performance of the proposed low IF system 500 and a direct down convert radar system. Then, experiments were conducted to demonstrate the capacity of measuring mechanical vibration using the low IF radar system 500. Finally, experiments for measuring human vital signs using the double sideband low IF system 500 were conducted.

The Comparison Between the Double Sideband Low IF System and the Direct Down Convert Radar System.

Figure 10A:
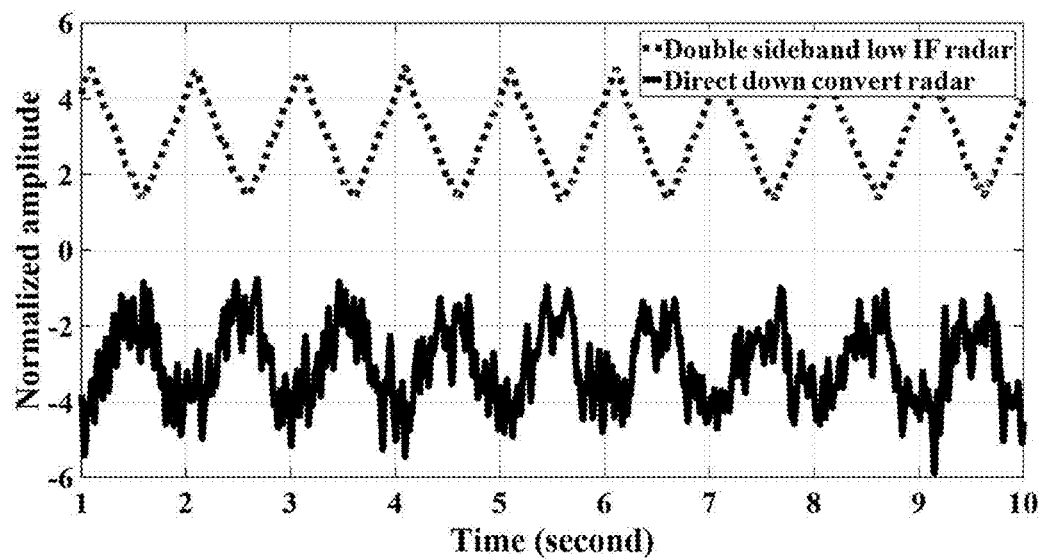
FIGS. 10A-10B, 11A-11B and 12A-12C are plots illustrating experimental comparisons of the double sideband low IF system of FIGS. 5A and 5B with other systems in accordance with various embodiments of the present disclosure.
Figure 10B:
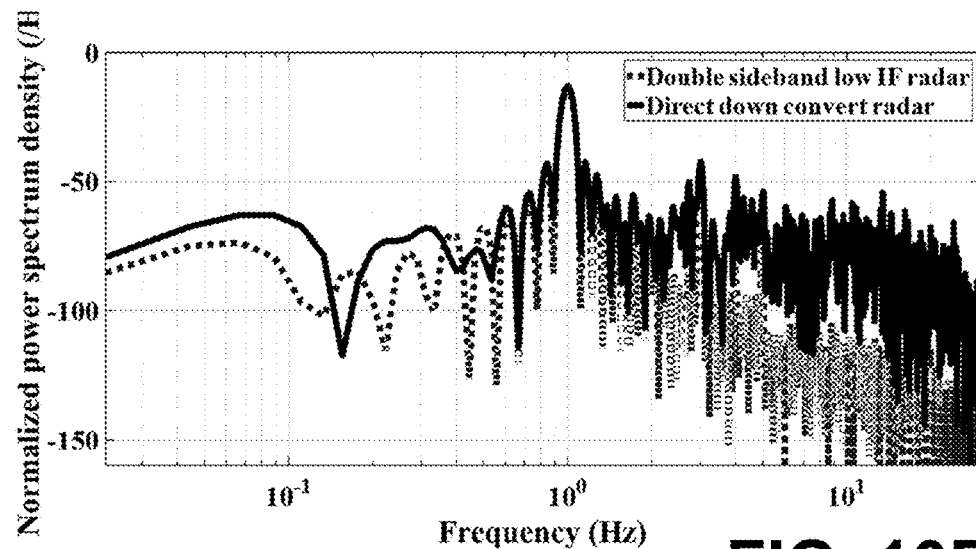

The comparison between the double sideband low IF system 500 and the direct down convert system can be seen in FIGS. 10A and 10B. FIG. 10A shows the measured baseband waveforms and FIG. 10B shows the power spectrum density of the baseband waveforms, with the waveforms normalized to 1 mm. Both systems were used to measure the mechanical vibration generated by an actuator. The actuator generated a periodic triangle wave vibration. The frequency of the vibration was 1 Hz and the peak-to-peak amplitude of the vibration was 3 mm. The distance between the radar and the actuator was fixed at 1 m for the experiment.

In FIG. 10A, the waveforms are offset from zero for the convenience of comparison. It can be seen from FIG. 10A that the measurement result from the double sideband low IF system 500 has a better SNR as compared to the waveform from the direct down convert system. This can be further verified in FIG. 10B, where the power spectrum density of the two waveforms are compared. In higher frequency range (>1 Hz), the noise level of the low IF system 500 is at least 10 dB lower than that of the direct down convert system. This result is consistent with the simulation results. From FIG. 10B, it can also be observed that the waveform of the direct down convert system has a higher power level near the DC frequency, corresponding to the distortion due to the DC offset from the mixer. The double sideband low IF system 500, since it down converts the RF signal to the IF frequency range, is insensitive to the DC offset and low frequency noise.

The Measurement of Mechanical Vibrations Using the Double Sideband Low IF Radar System.

Experiments were conducted to evaluate the performance of the double sideband low IF system 500 for vibration measurements. For the measurements, the actuator was set up 1 m away from the low IF radar system 500. The actuator generated a periodic triangle wave vibration. Multiple measurements were conducted under different vibration frequencies and amplitudes. The measurement data was processed with a 20-second window.

Figure 11A:
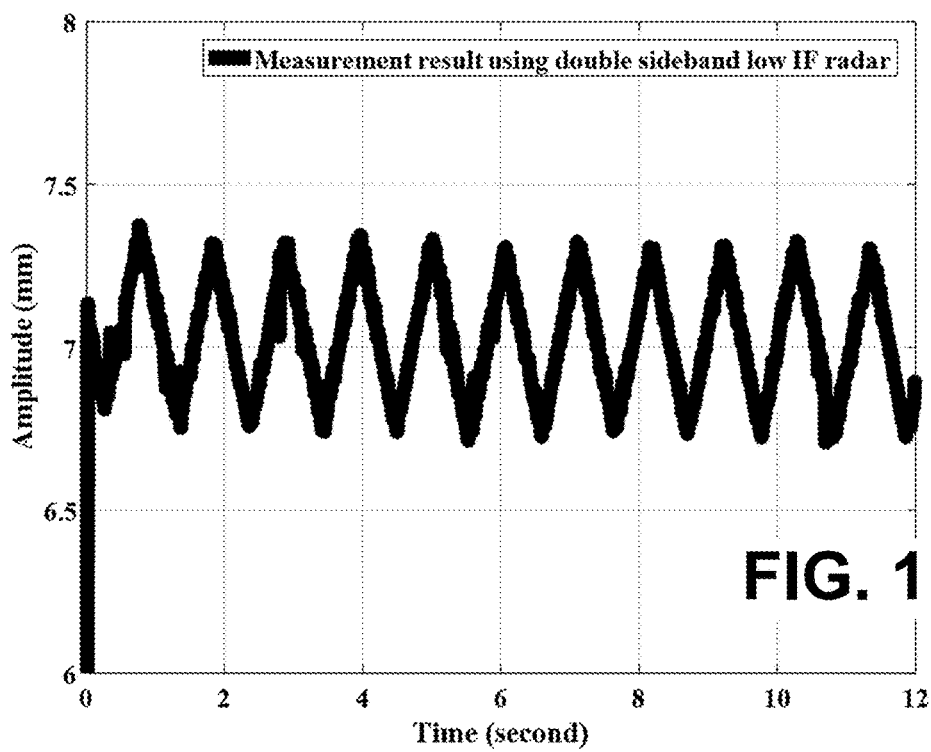
Figures 11B, 12A:
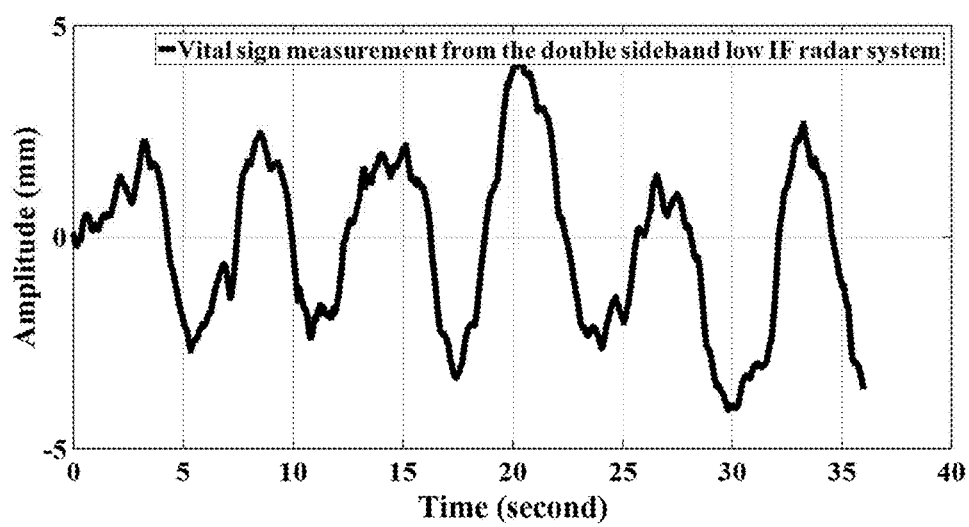

FIG. 11A shows an example of the measurement of a mechanical vibration using the double sideband low IF system 500. For this measurement, the peak-to-peak amplitude of the vibration was 0.5 mm, and the frequency was 1 Hz. It can be seen from FIG. 11A that the radar provides an accurate measurement result. The radar waveform is a triangle periodic signal with the expected amplitude and vibration frequency. The quantitative results of the measurements are shown in the table of FIG. 11B. Under different vibration conditions, the double sideband low IF system 500 can provide accurate estimations of both the frequency and the amplitude of the vibrations.

The Measurement of Human Vital Sign Using the Double Sideband Low IF Radar System.

Experiments were conducted to demonstrate the capacity of measuring human vital sign using the double sideband low IF system 500. During the measurements, the subjects sat about 1 m away from the vital sign radar. A contact sensor (e.g., a model 1010 piezoelectric pulse transducer) was attached to subjects' fingers to provide the reference heart rate. The waveform of the vital sign measurement data is shown in FIG. 12A. It can be seen that during the experiment, the subject breathed with a rate around 10 breath-per-minute. The displacement of the front chest was about 5 mm.

Figure 12B:
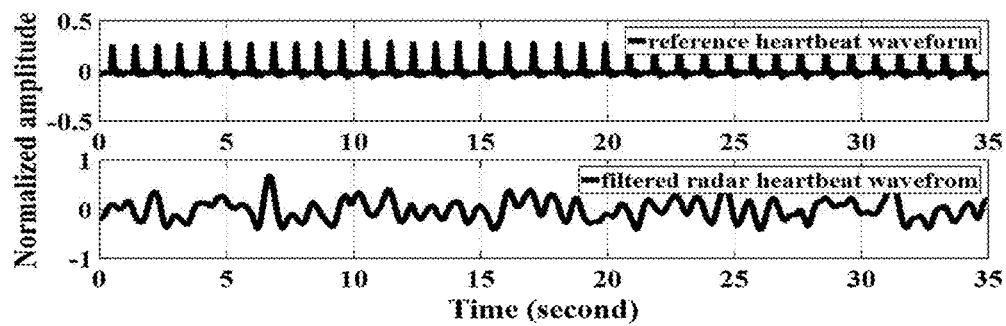
Figure 12C:
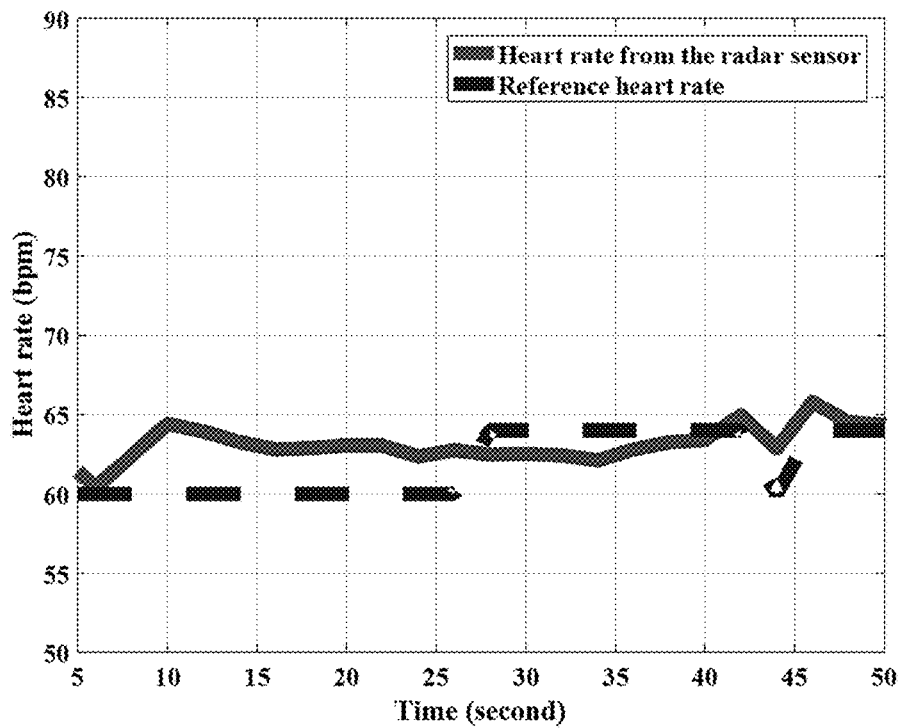

To further process the radar signal, a digital bandpass filter (0.7 Hz-1.5 Hz passband) was used to separate the heartbeat waveform from the noise and the respiration signal. The filtered radar heartbeat waveform and the reference heartbeat waveforms are shown in FIG. 12B. It can be seen that the filtered heartbeat waveform is consistent with the reference waveform from the contact sensor. The filtered heartbeat waveform was then transformed into frequency spectrum by FFT. The FFT was conducted with a 10-second measurement window. The heart rate was then estimated using the frequency spectrum. A 5-second incremental step size was used for the heart rate update. The estimated heart rate is shown in FIG. 12C. It can be seen that the double sideband low IF system 500 can provide an accurate heart rate estimation when compared to the reference heart rate. The average error of the measurement is 2.4 beat-per-minute (bpm).

In this disclosure, a double sideband low IF system was presented. The system was designed for noncontact mechanical vibration and vital sign measurement. The proposed radar architecture down converts RF signals to the IF frequency range, which helps to avoid the DC offset and lower the noise level. The system 500 uses a double sideband signal for transmission to allow the RF filter in the digitally assisted low IF system 100 to be removed from the transmitter side. By sampling the I/Q signals and the IF carrier simultaneously with an ADC, the architecture simplifies the synchronization mechanism. Simulations and experiments were conducted to evaluate the performance of the double sideband low IF system 500. Results showed that the system 500 can provide accurate measurements on low frequency mechanical vibrations and human vital sign.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A transceiver system, comprising:
   transmit circuitry configured to transmit a modulated signal at a target, the modulated signal generated by modulating a local oscillator (LO) signal with an intermediate frequency (IF) carrier;
   receive circuitry configured to generate an IF signal by down converting a received signal with the LO signal, the received signal comprising backscatter of the modulated signal from the target;
   an analog-to-digital converter (ADC) configured to simultaneously sample the IF carrier and the IF signal; and
   processing circuitry configured to determine a vibration frequency of the target by demodulating the sampled IF signal with the sampled IF carrier.

2. The transceiver system of claim 1, wherein the transmit circuitry comprises a transmit mixer configured to modulate the LO signal with the IF carrier.

3. The transceiver system of claim 1, wherein the receive circuitry comprises a receive mixer configured to down convert the received signal with the LO signal.

4. The transceiver system of claim 1, comprising a voltage controlled oscillator (VCO) that generates the LO signal.

5. The transceiver system of claim 4, wherein the LO signal is about 5.8 GHz.

6. The transceiver system of claim 1, comprising an intermediate frequency oscillator (IFO) that generates the IF carrier.

7. The transceiver system of claim 6, wherein the IF carrier is about 70 MHz.

8. The transceiver system of claim 1, wherein the ADC samples the IF carrier and the IF signal at a sampling frequency of about 10 kHz.

9. The transceiver system of claim 1, wherein the target is a person and the vibration frequency corresponds to a vital sign of the person.

10. A method, comprising:
    generating a modulated signal by modulating a local oscillator (LO) signal with an intermediate frequency (IF) carrier;
    transmitting the modulated signal at a target;
    receiving a received signal comprising backscatter of the modulated signal from the target;
    generating an IF signal by down converting the received signal with the LO signal;
    generating a sampled IF signal and a sampled IF carrier by simultaneously sampling the IF carrier and the IF signal; and
    determining a vibration frequency of the target by demodulating the sampled IF signal with the sampled IF carrier.

11. The method of claim 10, wherein the LO signal is modulated with the IF carrier by a transmit mixer.

12. The method of claim 10, wherein the received signal is down converted with the LO signal by a receive mixer.

13. The method of claim 10, comprising generating the LO signal with a voltage controlled oscillator (VCO).

14. The method of claim 13, wherein the LO signal is about 5.8 GHz.

15. The method of claim 10, comprising generating the IF carrier with an intermediate frequency oscillator (IFO).

16. The method of claim 15, wherein the IF carrier is about 70 MHz.

17. The method of claim 10, wherein the IF carrier and the IF signal are simultaneously sampled at a sampling frequency of about 10 kHz.

18. The method of claim 10, wherein the target is a person and the vibration frequency corresponds to a vital sign of the person.

19. The method of claim 18, wherein the vital sign is heart rate and respiration rate.

20. The method of claim 10, comprising bandpass filtering the IF carrier and the IF signal prior to sampling.

* * * * *